(12) United States Patent
Firoozabadi et al.

(10) Patent No.: US 11,576,585 B2
(45) Date of Patent: Feb. 14, 2023

(54) ARTIFACT-TOLERANT PULSE RATE VARIABILITY MEASUREMENT

(71) Applicant: KONINKLIJKE PHILIPS N.V., Eindhoven (NL)

(72) Inventors: Reza Firoozabadi, Thousand Oaks, CA (US); Saeed Babaeizadeh, Arlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 469 days.

(21) Appl. No.: 16/604,616

(22) PCT Filed: Apr. 18, 2018

(86) PCT No.: PCT/EP2018/059949
§ 371 (c)(1),
(2) Date: Oct. 11, 2019

(87) PCT Pub. No.: WO2018/192997
PCT Pub. Date: Oct. 25, 2018

(65) Prior Publication Data
US 2021/0113104 A1  Apr. 22, 2021

Related U.S. Application Data

(60) Provisional application No. 62/486,967, filed on Apr. 18, 2017.

(51) Int. Cl.
*A61B 5/00* (2006.01)
*A61B 5/024* (2006.01)
*A61B 5/318* (2021.01)

(52) U.S. Cl.
CPC ...... *A61B 5/02416* (2013.01); *A61B 5/02405* (2013.01); *A61B 5/318* (2021.01); *A61B 5/7221* (2013.01); *A61B 5/7278* (2013.01)

(58) Field of Classification Search
CPC ............ A61B 5/02405; A61B 5/02416; A61B 5/02438; A61B 5/318; A61B 5/7207; A61B 5/7221; A61B 5/7278
See application file for complete search history.

(56) References Cited

U.S. PATENT DOCUMENTS

| | | |
|---|---|---|
| 2005/0038349 A1 | 2/2005 | Choi et al. |
| 2013/0079606 A1 | 3/2013 | McGonigle et al. |
| 2013/0345569 A1 | 12/2013 | Mestha et al. |

OTHER PUBLICATIONS

"Task Force of The European Society of Cardiology and The North American Society of Pacing and Electrophysiology (Membership of the Task Force listed in the Appendix)", Heart rate variability, European Heart Journal (1996) 17, 354-381.

(Continued)

*Primary Examiner* — Mark D Remaly

(57) ABSTRACT

A PPG PRV device for generating a PRV parameter of a PPG signal (20) as an estimation of a HRV parameter of an ECG signal. The PPG PRV device employs a PPG probe (700) and a PPG PRV controller (710). In operation, the PPG probe (700) generate a PPG signal (20). In response thereto, the PPG PRV controller (710) generates a normalized PPG signal (20') including a plurality of pulses of the PPG signal (20) designated as normal pulses by the PPG PRV controller (710) and excluding at least one pulse of the PPG signal (20) designated at least one abnormal pulse by the PPG PRV controller (710), wherein the normalized PPG signal (20') is HRV comparable to the ECG signal. The PPG PRV controller (710) derives the PRV parameter from a HRV measurement of the normalized PPG signal (20').

20 Claims, 17 Drawing Sheets

(56) References Cited

OTHER PUBLICATIONS

Lu, G. et al., "Limitations of Oximetry to Measure Heart Rate Variability Measures", Cardiovascular Engineering 9 (3):119-25, Oct. 2009.

International Search Report and Written Opinion, International Application No. PCT/EP2018/059949, dated Jul. 3, 2018.

ARTIFACT-TOLERANT PULSE RATE VARIABILITY MEASUREMENT

This application is the U.S. National Phase application under 35 U.S.C. § 371 of International Application No. PCT/EP2018/059949, filed on 18 Apr. 2018, which claims the benefit of U.S. Provisional Application No. 62/486,967, filed 18 Apr. 2017. These applications are hereby incorporated by reference herein.

TECHNICAL FIELD

The inventions of the present disclosure generally relate to measuring pulse rate variability (PRV) as an estimation of heart rate variability (HRV), and more particularly to systems, devices and methods for measuring pulse rate variability using photoplethysmography (PPG) technology.

BACKGROUND

Use of wearable devices capable of collection and analysis of physiological parameters is rapidly increasing. Although electrocardiogram (ECG) is generally considered to be the standard tool to monitor cardiac health, an ECG is methodologically difficult to record and analyze using wearable devices. As an alternative to ECG monitoring, photoplethysmography (PPG) technology used in wearable devices makes it possible to use them as portable health monitoring tools for measuring the clinical parameters such as pulse rate, oxygen saturation, respiration, and a number of other features in a non-invasive manner. These PPG devices use optical sensors to detect the blood volume changes by amount of either transmitted light (e.g., via a fingertip application) or reflection light (e.g., via a wrist application).

More particularly, an important feature to measure in cardiac monitoring is heart rate variability (HRV), which is defined by the variation in interbeat intervals between successive beats. As known in the art of the present disclosure (See, e.g., Task Force of the European Society of Cardiology and the North American Society of Pacing and Electrophysiology: Heart rate variability. Standards of measurement, physiological interpretation and clinical use. European Heart Journal, 17, 1996, s. 354-381), HRV is clinically significant as the vascular system is regulated by autonomic nervous system and a reduction in a value of HRV relates to several cardiological and non-cardiological diseases (e.g., myocardial infarction, diabetic neuropathy, myocardial dysfunction and tetraplegia). Furthermore, a reduction in a value of HRV has been seen in patients with cardiac transplantation.

Calculating HRV needs accurate measurement of interbeat intervals which is more reachable in ECG beats with the sharp r-wave peaks than PPG pulses with smooth shape, but the practical issues in collecting ECG by wearable devices has motivated the inventors of the present disclosure to calculate pulse rate variability (PRV) in PPG technology as an estimation of HRV.

However, as known in the art of the present disclosure (See, G. Lu, F. Yang, Limitations of oximetry to measure heart rate variability measures, Cardiovasc Eng. 9:119-125, 2009), measuring the pulse rate variability (PRV) using PPG technology needs highly accurate measurements, which is challenging due to several inherent characteristics of PPG pulses such as the pulse smoothness, and further due to PPG pulses being imposed to higher levels of artifact with the bandwidth overlapping the underlying PPG spectrum. Utilization of an accelerometer-based motion sensor with PPG technology may help to detect the artifact-corrupted pulses more conveniently, but those sensors are not always available for artifact detection. Thus, the art of the present disclosure teaches away from using PPG technology as an estimation of HRV of ECG signals.

SUMMARY

The inventions of the present disclosure are directed to an approach to measure pulse rate variability (PRV) parameters in a single-channel PPG without a need for any additional sensor (e.g., an accelerometer) based upon a detection and a removal of the abnormal pulses of a PPG signal whereby the PPG-based PRV parameters are comparable to heart rate variability (HRV) parameters of simultaneous ECG recordings. The inventions of the present disclosure provide and describe systems, devices and methods for estimating heart rate HRV parameters by analyzing a single channel of PPG.

One exemplary embodiment of the inventions of the present disclosure is a PPG PRV device for generating a PRV parameter of a PPG signal as an estimation of a HRV parameter of an ECG signal. The PPG PRV device employs a PPG probe and a PPG PRV controller. In operation, the PPG probe generate a PPG signal. In response thereto, the PPG PRV controller generates a normalized PPG signal including a plurality of pulses of the PPG signal designated as normal pulses by the PPG PRV controller and excluding one or more pulses of the PPG signal designated as abnormal pulse(s) by the PPG PRV controller, wherein the normalized PPG signal is HRV comparable to the ECG signal. The PPG PRV controller derives the PRV parameter from a HRV measurement of the normalized PPG signal.

In a second exemplary embodiment of the inventions of the present disclosure, the PPG PRV controller employs a PPG signal normalizer for generating the normalized PPG signal including the plurality of pulses of the PPG signal designated as normal pulses by the PPG signal normalizer and excluding the one or more pulses of the PPG signal designated the abnormal pulse(s) by the PPG signal normalizer, wherein the normalized PPG signal is HRV comparable to the ECG signal. The PPG PRV controller for employs a PRV parameter analyzer for deriving the PRV parameter from a HRV measurement of the normalized PPG signal.

In a third exemplary embodiment of the inventions of the present disclosure, a PPG PRV method for generating a PRV parameter of a PPG signal as an estimation of a HRV parameter of an ECG signal involves a PPG PRV controller generating a normalized PPG signal including a plurality of pulses of the PPG signal designated as normal pulses by the PPG PRV controller and excluding one or more pulses of the PPG signal designated as abnormal pulse(s) by the PPG PRV controller, wherein the normalized PPG signal is HRV comparable to the ECG signal. The PPG PRV method further involves the PPG PRV controller deriving the PRV parameter from a HRV measurement of the normalized PPG signal.

For purposes of describing and claiming the inventions of the present disclosure, (1) terms of the art of the present disclosure including, but not limited to, "photoplethysmography (PPG)", "pulse rate variability (PVR)", "electrocardiogram "ECG" and "heart rate variability (HRV)", are to be interpreted as understood in the art of the present disclosure and as exemplary described herein;

(2) the term "PPG device" broadly encompasses all devices, known prior to and subsequent to the present disclosure, for collecting one channel of PPG waveform, and the term "PPG PRV" device broadly encompasses all PPG devices incorporating the inventive principles of the present disclosure as exemplary described herein for generating a PRV parameter of a PPG signal as an estimation of a HRV parameter of an ECG signal. Examples of a "PPG device" include, but are not limited to Philips Intellivue Guardian Solution with wearable wireless patch, activity monitoring watches (e.g., Actiwatch and HealthWatch) and home sleep monitoring devices (e.g., Alice PDx). This list of devices and related applications is in no way intended to be limiting, but rather just provided to be a sample and example of the types of devices and applications in/with which exemplary embodiments of the present disclosure can be used, including devices and applications known today and to be known in the future;

(3) the term "PPG method" broadly encompasses all methods, known prior to and subsequent to the present disclosure, for collecting one channel of PPG waveform, and the term "PPG PRV method" device broadly encompasses all PPG methods incorporating the inventive principles of the present disclosure as exemplary described herein for generating a PRV parameter of a PPG signal as an estimation of a HRV parameter of an ECG signal;

(4) the term "HRV measurement" broadly encompasses all techniques, know prior to and subsequent to the present disclosure for calculating a HRV parameter of a ECG signal. Examples of a HRV measurement include, but are not limited to, time-domain parameters as known in the art of the present disclosure (e.g., SDNN, pNN50, RMSSD, SDSD, NN50), frequency-domain parameters as known in the art of the present disclosure (e.g., ULF, VLF, LF, HF, LF/HF) and non-linear parameters as known in the art of the present disclosure (e.g., Poincare plot, sample entropy);

(5) the term "HRV comparable" broadly encompasses a PPG signal normalized in accordance with the inventive principles of the present disclosure as exemplary described herein whereby a HRV measurement of the PPG signal generates a PRV parameter corresponding/equivalent to a HRV parameter generated by a HRV measurement of a ECG signal;

(6) an exclusion of an abnormal pulse from a PPG signal broadly encompasses an exclusion of an interval preceding and/or succeeding a pulse of a PPG signal;

(6) the term "controller" broadly encompasses all structural configurations, as understood in the art of the present disclosure and as exemplary described in the present disclosure, of an application specific main board or an application specific integrated circuit for controlling an application of various inventive principles of the present disclosure as exemplary described in the present disclosure. The structural configuration of the controller may include, but is not limited to, processor(s), computer-usable/computer readable storage medium(s), an operating system, application module(s), peripheral device controller(s), slot(s) and port(s);

(7) the term "application module" broadly encompasses a component of a controller including an electronic circuit and/or an executable program (e.g., executable software and/or firmware stored on non-transitory computer readable medium(s)) for executing a specific application. Any descriptive labeling of an application module herein (e.g., a "PPG probe activator" module, "PPG signal normalizer" module and a "PRV parameter analyzer") serves to identify a particular application module as described and claimed herein without specifying or implying any additional limitation to the term "application module"; and (8) the term "signal" broadly encompasses all forms of a detectable physical quantity or impulse (e.g., voltage, current, or magnetic field strength) as understood in the art of the present disclosure and as exemplary described herein for communicating information in support of applying various inventive principles of the present disclosure as subsequently described herein. Any descriptive labeling for the term "signal" herein facilitates a distinction between signals as described and claimed herein without specifying or implying any additional limitation to the term "signal".

The foregoing embodiments and other embodiments of the inventions of the present disclosure as well as various features and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

DETAILED DESCRIPTION

The present disclosure provides novel and nonobvious systems, devices and methods for estimating heart rate variability (HRV) parameters by analyzing a single-channel PPG, where abnormal pulses of the single-channel PPG are detected and excluded from the PPG signal before a PRV analysis of the interbeat intervals. More particularly, for an accurate PRV analysis of the interbeat intervals, abnormalities of the PPG signal must be detected and excluded from the PRV analysis in accordance with the present disclosure, such as pulses of the PPG signal caused by motion artifact and arrhythmic cardiac beats (e.g., premature ventricular contractions (PVC) and premature atrial contractions (PAC)).

Figure 1:
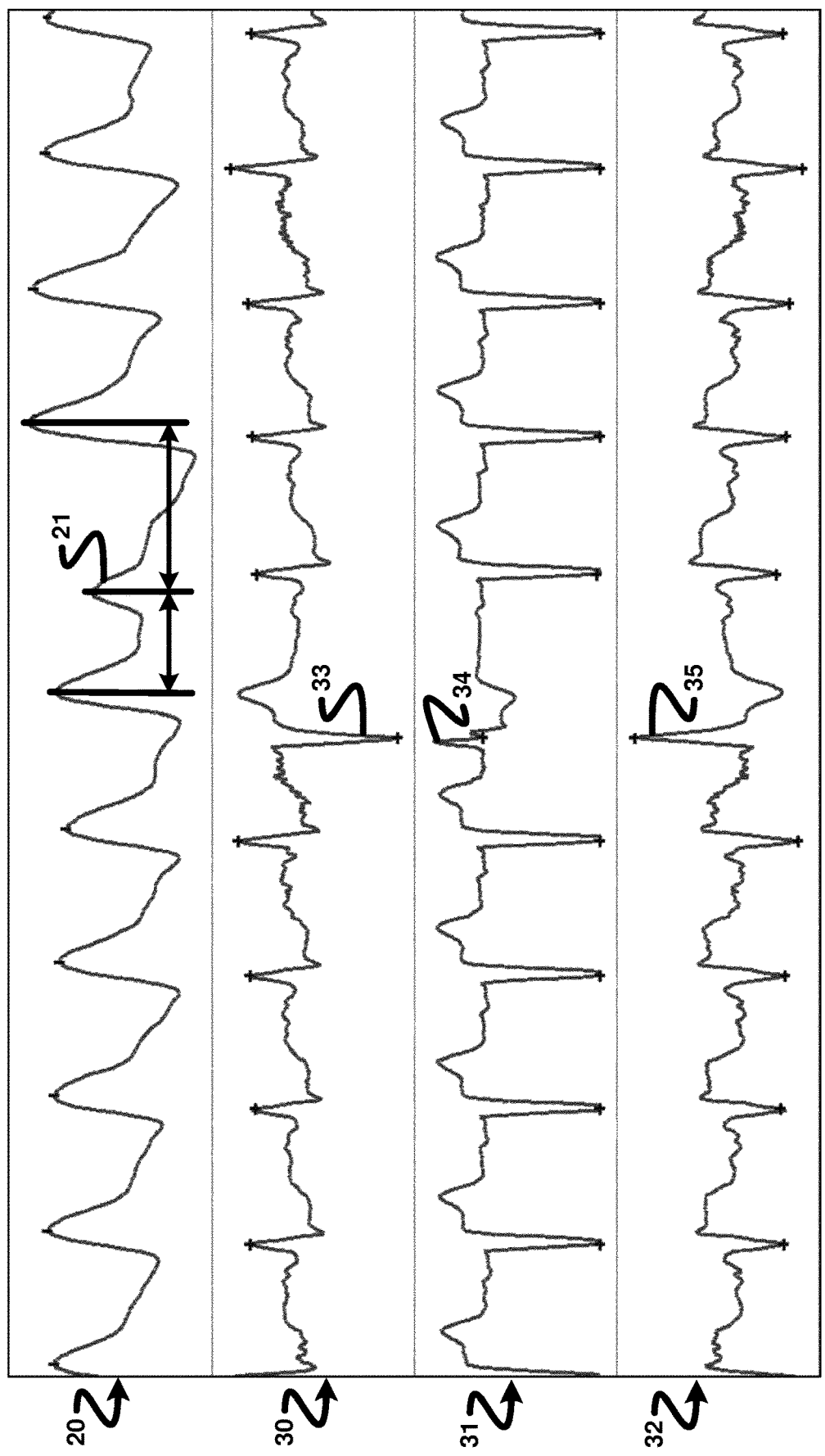
FIG. 1 illustrates an exemplary exclusion from a pulse rate variability (PRV) of a photoplethysmography (PPG) signal in accordance with the inventive principles of the present disclosure of interbeat intervals preceding and succeeding an abnormal PPG pulse caused by an arrhythmia.

For example, FIG. 1 shows a PPG signal 20, a ECG lead II channel 30, a ECG lead V channel 31 and a ECG lead aVR channel 32 whereby an abnormal pulse 21 of PPG channel 20 caused by a PVC is delayed from abnormal pulses 33, 34 and 35 of respective ECG signals 30, 31 and 32 also caused by the PVC. In accordance with the present disclosure, to transform the PPG signal 20 into a HRV comparable signal with the corresponding ECG signal, the intervals immediately preceding and/or immediately succeeding abnormal PPG pulse 20 (as symbolized by the bi-directional arrows) caused by arrhythmia (PVC) must be detected and excluded from the PRV analysis of the PPG signal.

Figure 2:
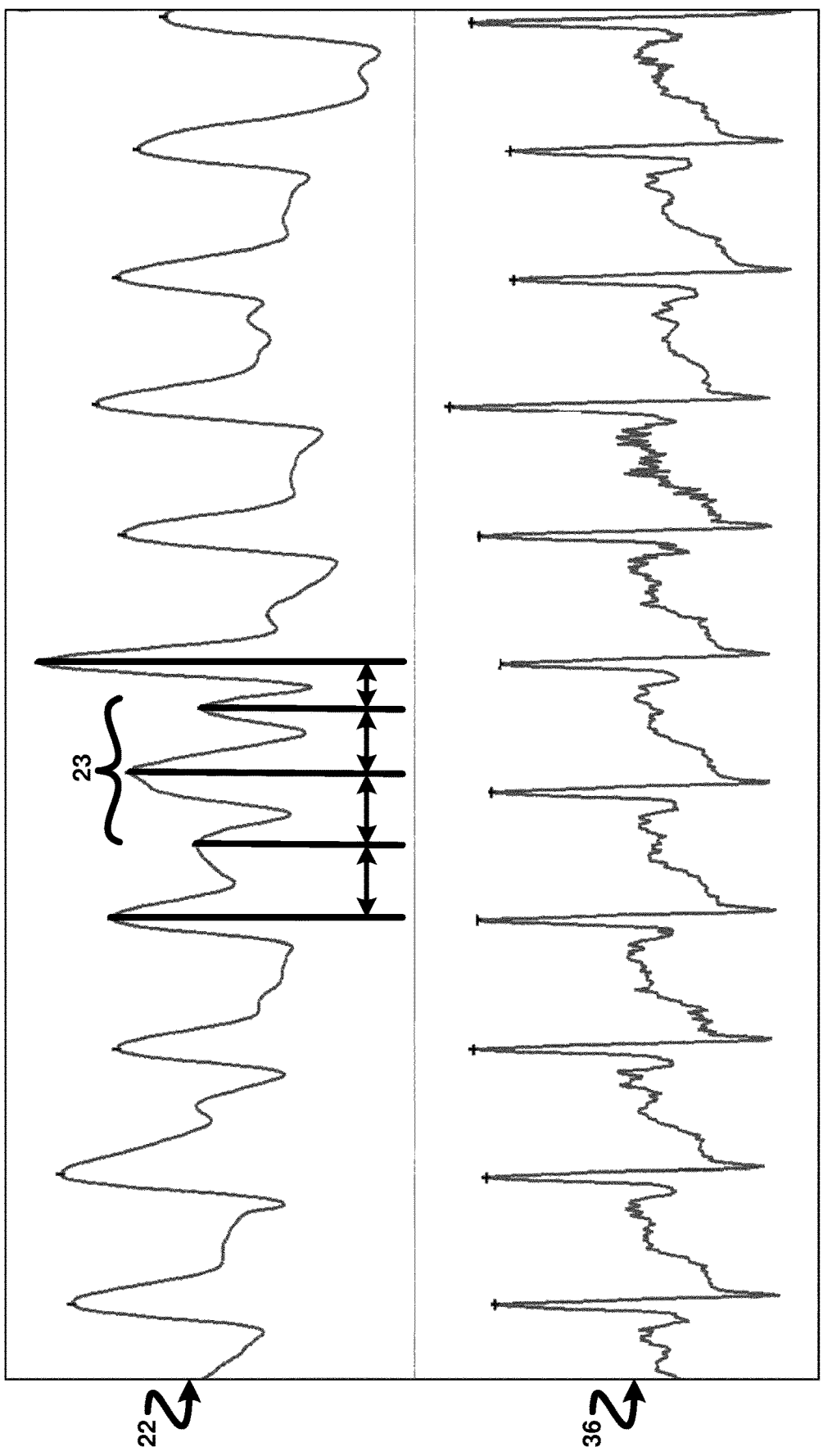
FIG. 2 illustrates an exemplary exclusion from a PRV of a PPG signal in accordance with the inventive principles of the present disclosure of interbeat intervals preceding and succeeding three (3) abnormal PPG pulses caused by an artifact.

By further example, FIG. 2 shows a PPG channel 20 and a ECG lead II channel 36 whereby a sequence of three (3) abnormal pulses 23 caused by an artifact appearing in random points in time. In accordance with the present disclosure, to transform the PPG signal 22 into a HRV comparable signal with the corresponding ECG signal, the intervals immediately preceding and/or immediately succeeding abnormal PPG pulse 20 (as symbolized by the bi-directional arrows) are deviated from the average interbeat interval and should be discarded and not included in the PRV analysis of the PPG signal.

To facilitate an understanding of the various inventions of the present disclosure, the following description of FIGS. 3-16 teaches basic inventive principles of various methods for generating a PRV parameter of a PPG signal as an estimation of a HRV parameter of an ECG signal in accordance with the present disclosure. From this description, those having ordinary skill in the art will appreciate how to apply the inventive principles of the present disclosure of additional embodiments of methods for generating a PRV parameter of a PPG signal as an estimation of a HRV parameter of an ECG signal in accordance with the present disclosure.

Figure 3:
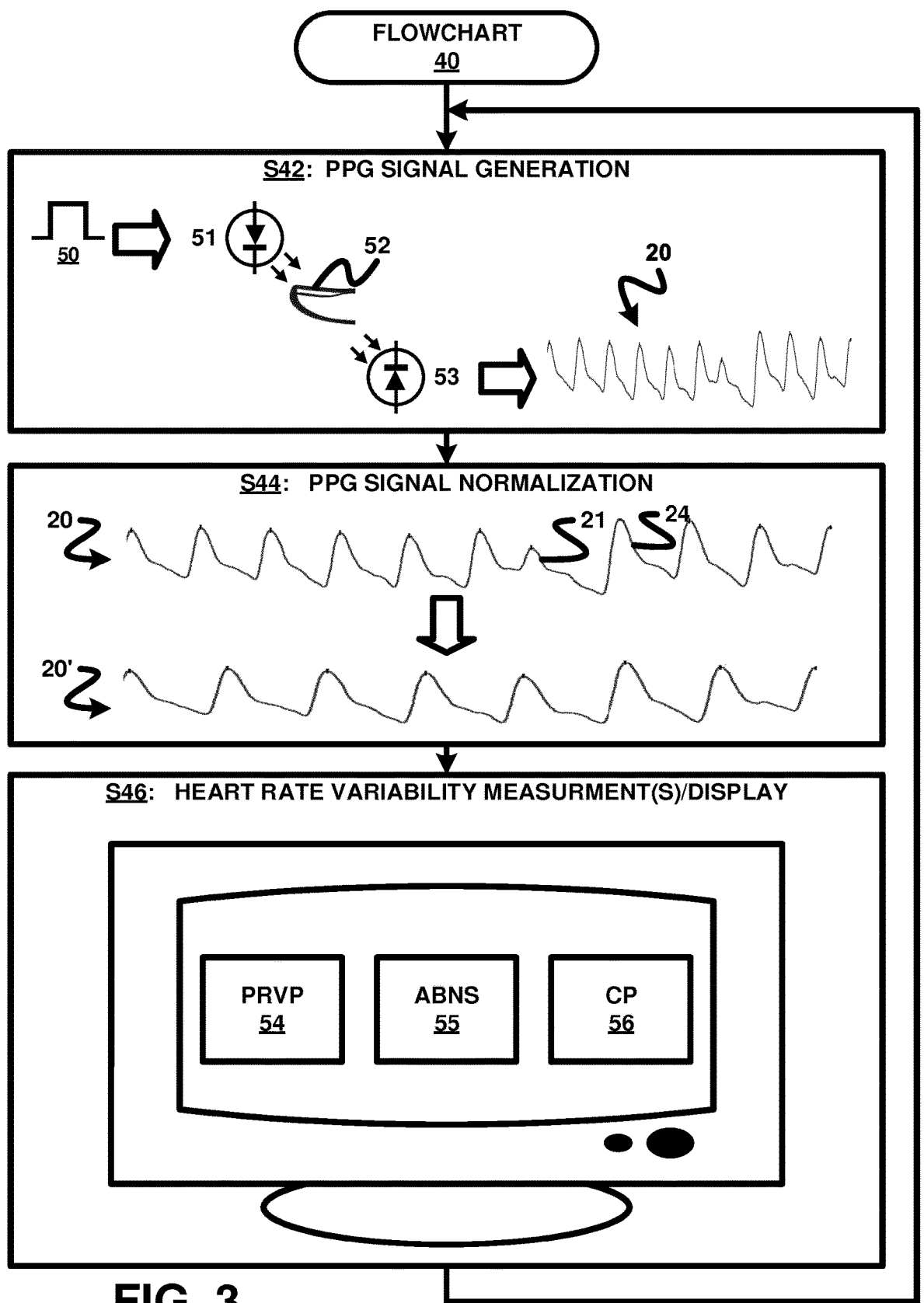
FIG. 3 illustrates a flowchart representative of an exemplary embodiment of a PPG PRV method in accordance with the inventive principles of the present disclosure.

FIG. 3 illustrates a flowchart 40 representative of an embodiment of a PPG PRV method of the present disclosure. Referring to FIG. 3, a stage S42 of flowchart 40 encompasses a generation of a PPG signal. In practice, the PPG signal may be generated by any technique as known in the art of the present disclosure. In one embodiment as shown in stage S42, an activation signal 50 is applied to a light emitter 51 (e.g., an infrared LED) where light transmitted through an anatomy (e.g., a finger 52 as shown, or a ear or forehead) is received by a light detector 53 (e.g., a photodiode) to thereby generate a PPG signal 20.

A stage S44 of flowchart 40 encompasses a normalization of PPG signal 20 by an exclusion of pulses of PPG signal 20 designated as abnormal, such as, for example, a designated abnormal pulse 21 to thereby yield a normalized PPG signal 20' that is HRV comparable to a ECG signal. Optionally, any normal pulses immediately succeeding a designated abnormal pulse of PPG signal 20 may also be excluded, such as, for example, a designated normal pulse 24. Embodiments of stage S44 will be further described herein in connection with the description of FIG. 4.

A stage S46 of flowchart 40 encompasses a HRV measurement of the normalized PPG signal 20' to yield a PRV parameter 54 for display. Optionally, an abnormality score 55 and a coverage percentage may also be generated and displayed. Embodiments of stage S46 will be further described herein in connection with the description of FIG. 4.

Figure 4:
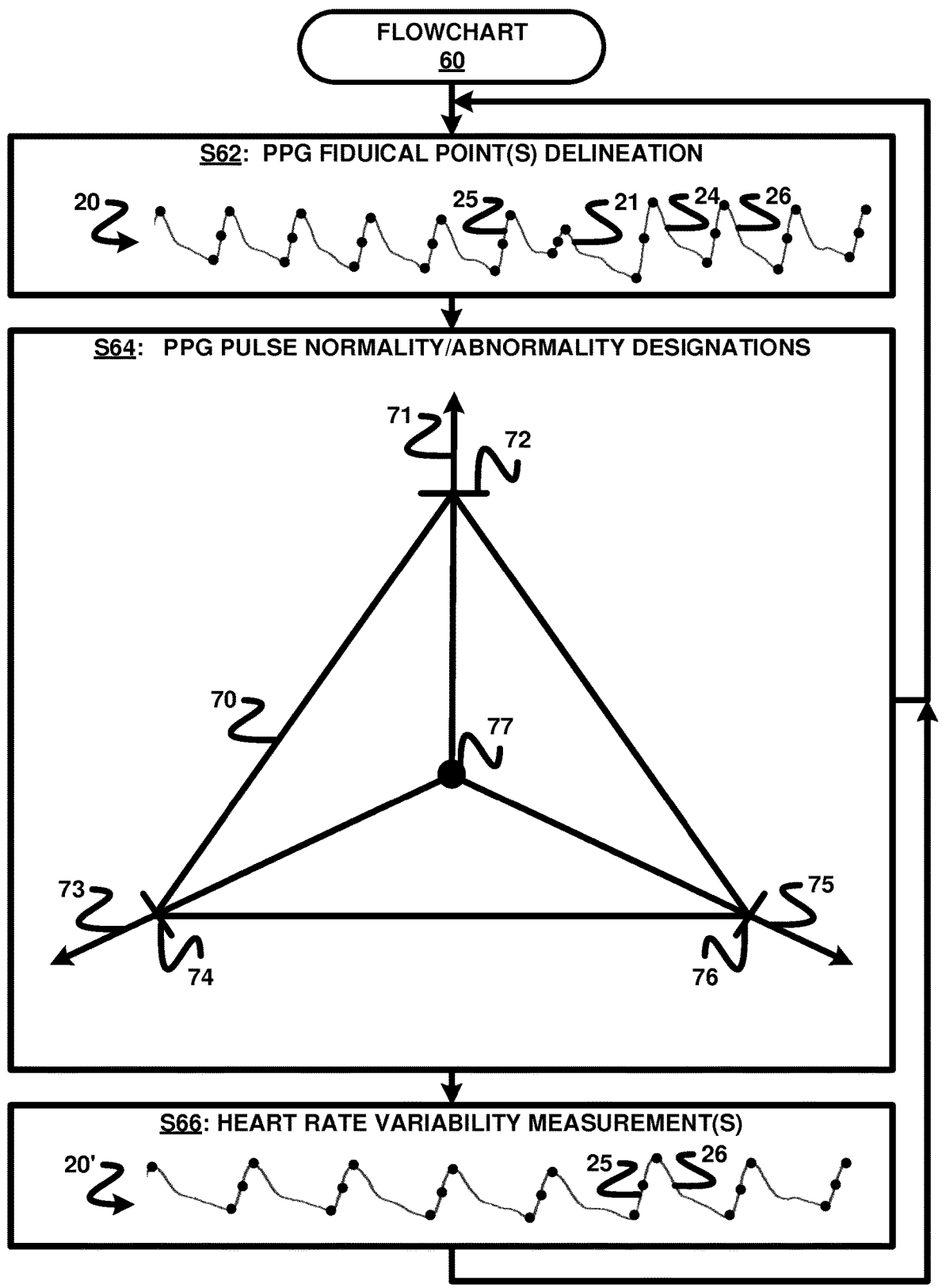
FIG. 4 illustrates a flowchart representative of a first exemplary embodiment of a the PPG PRV method of FIG. 3 in accordance with the inventive principles of the present disclosure.

FIG. 4 illustrates a flowchart 60 representative of an embodiment of the PPG PRV method of FIG. 3. Referring to FIG. 4, a stage S62 of flowchart 60 encompasses a delineation of fiducial point for each pulse of a sequence of pulses for a PPG signal, such as, for example, a delineation of fiducial points of a PPG signal 20 symbolized as block dots as shown in FIG. S62.

After reaching a specific number of delineated pulses, a stage S64 of flowchart 60 encompasses a normality/abnormality designation of each delineated pulse of the PPG signal. In practice, any technique for detecting abnormal pulses of a PPG signal due to arrhythmia, artifacts, etc. may be employed during stage S64.

In one embodiment as shown in stage S64, to detect the level of abnormality, 3-dimensional 'Abnormality Score' is assigned to each PPG pulse. The 'Abnormality Score'" consists of 'interbeat interval deviation' 71, an 'amplitude ratio' 73, and 'abnormal pulse proximity' elements 74. The abnormal pulses corrupted by artifact or the arrhythmia are eliminated using criteria on these scores with 3 thresholds defined as interbeat interval deviation threshold (T) 72 which is maximum acceptable deviation of interbeat interval from its running average, an amplitude ratio threshold (M) 74 which is the maximum acceptable ratio of pulse amplitude over its running average (or its inverse if the ratio is less than 1), and normal pulse segment threshold (N) 76 which is the minimum number of consecutive normal intervals. The thresholds can be adjusted manually or automatically. Stage S64 shows a graphical range 70 of the Abnormality Score' defined by the threshold relative to an origin 77.

In one embodiment, interbeat interval deviation 71 is measured in milliseconds starting at 100 ms with an interbeat interval deviation threshold (T) 72 of 200 ms, pulse amplitudes are measured in millivolts with amplitude ratio threshold (M) 74 of 3, and normal pulse segment threshold (N) 76 may be 3.

Stage S64 may further define a 'Coverage Percentage' to show the percentage of normal pulses analyzed by the algorithm against all detected pulses. Adjusting the thresholds will change the coverage percentage in addition to PRV. Optimal thresholds will be determined by compromising the coverage percentage and the agreement of PRV with a reference ECG-derived HRV as will be further described in the present disclosure.

A stage S66 of flowchart 60 encompasses a HRV measurement of the normalized PPG signal 20' from stage S64 based on the fiducial points.

Figure 5:
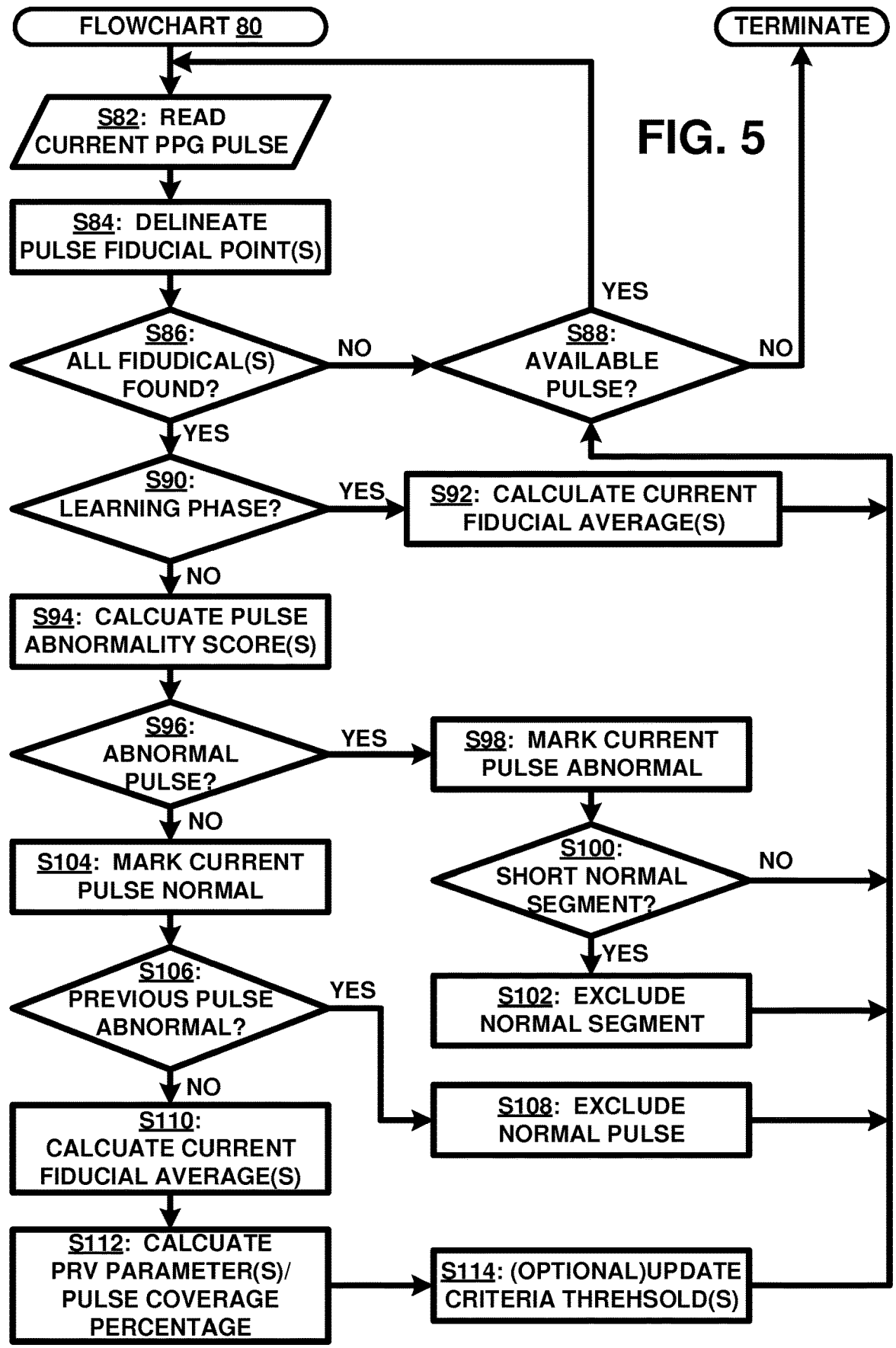
FIG. 5 illustrates a flowchart representative of a second exemplary embodiment of a PPG PRV method of FIG. 3 in accordance with the inventive principles of the present disclosure.

FIG. 5 illustrates a flowchart 80 representative of an embodiment of flowchart 60 (FIG. 4). Flowchart 80 incorporates a fiducial point detector including the trough, upslope and peak points on each PPG pulse. These points are then verified to be valid with respect to their relative amplitude.

Figure 6:
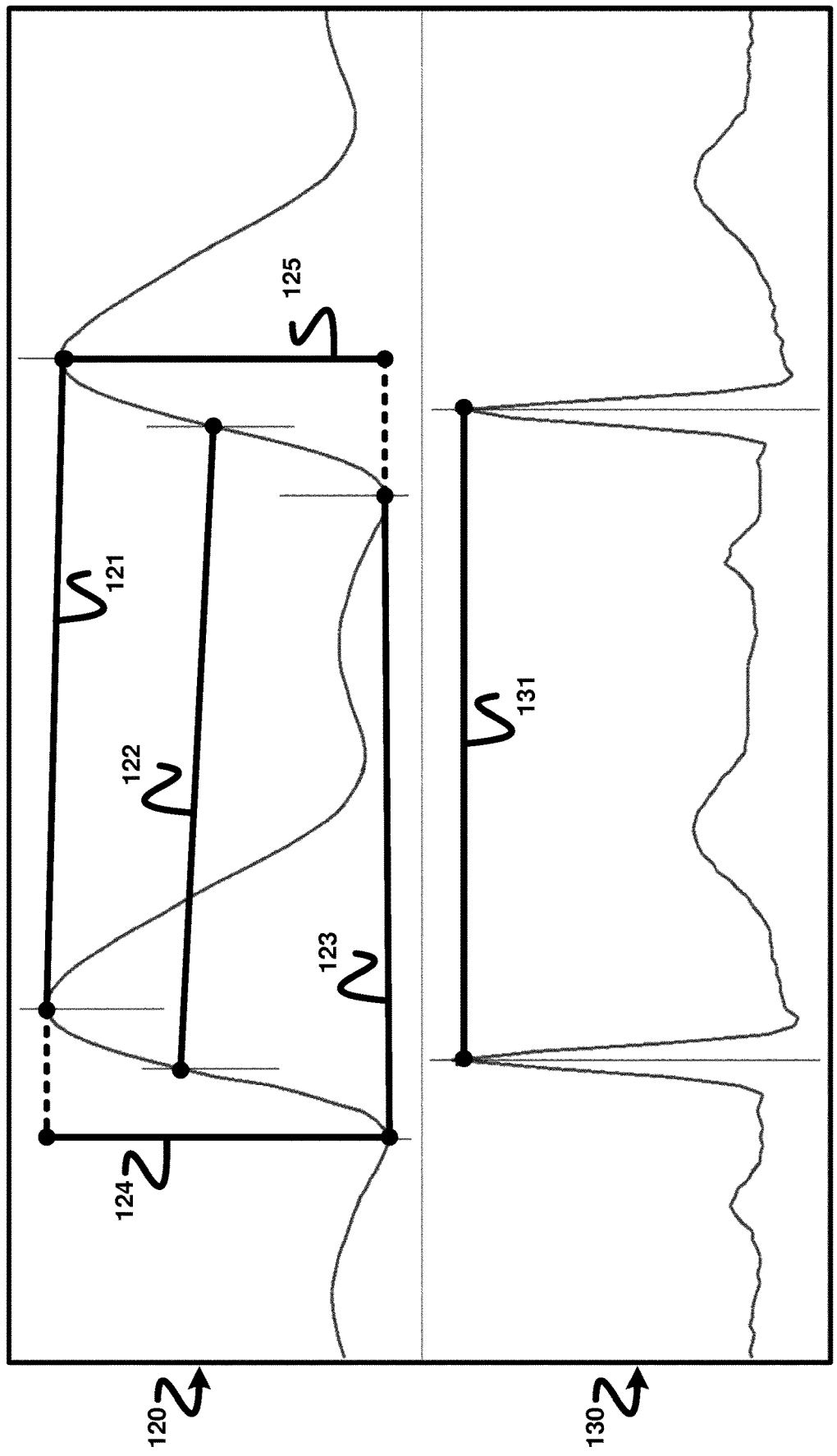
FIG. 6 illustrates exemplary fiducial points of a PPG signal in accordance with the inventive principles of the present disclosure.

For example, FIG. 6 illustrates two three intervals between successive PPG pulses 120 including a peak-peak interval 121 extending between peak fiducial points of the PPG pulses 120, an upslope-upslope 122 extending between upslope fiducial points of the PPG pulses 120 and a trough-trough interval 123 extending between trough fiducial points of the PPG pulses 120. The PPG interbeat interval is defined as the median of these three intervals. Peak-Trough (PT) amplitudes 124 and 125 for each pulse is also shown. For comparison purposes, comparable ECG interbeat interval 131 (distance between normal R-wave peaks) is shown.

Using the detected fiducial points, flowchart 80 provides for a measurement of a number of parameters from the PPG signal waveform for each pulse. One of these parameters is Interbeat Interval (IBI) which is the median of three (3) other intervals between the succeeding PPG pulses: Peak-Peak interval 121, Upslope-Upslope interval 122, and Trough-Trough interval 123 of FIG. 6. The PPG interbeat interval is defined as median of these three intervals:

$$IBI = \text{median}(T_{PP}, T_{UU}, T_{TT})$$

The Peak-Trough amplitude ($PT_{ampl}$) is the parameter which measures the height of each pulse from the lowest point to the highest point as exemplary shown in FIG. 6.

The third parameter is the distance of current pulse from the most recent abnormal pulse which is the number of normal pulses in between. The pulses farther from abnormal pulses are more reliable.

A learning phase of flowchart 80 relates to the analysis of a number of initial pulses and calculates only the initial averages for IBI and $PT_{ampl}$. For the pulses not in the learning phase, abnormality scores are calculated and used in the abnormality criteria to decide the normality or abnormality of the current pulse. If the pulse is marked abnormal and there is a short interval of continuous normal pulses before this pulse with the length<N pulses, the segment is eliminated and calculations in the segment are excluded. N is one of the configurable thresholds in the algorithm.

If the pulse is marked normal and follows an abnormal pulse (the first normal beat), it is excluded and no more calculation is performed, otherwise the averages for IBI and $PT_{ampl}$ are updated, PRV parameters are calculated, and the Coverage Percentage is measured. In an optional step, the thresholds are updated manually or automatically based on the abnormality score and the coverage percentage.

Abnormality criteria in accordance with flowchart 80:

One exemplary embodiment of the present disclosure uses the following criteria to detect the abnormal pulses and exclude them from analysis:

1. Amplitude Ratio:

$$R = \begin{cases} PT/PT_{avg}, & PT > PT_{avg} \\ PT_{avg}/PT, & \text{otherwise} \end{cases}$$

If R>M (M is the amplitude ratio threshold), the pulse is abnormal.

2. Interbeat Interval Deviation:

$$\Delta = |IBI - IBI_{avg}|$$

If $\Delta > T$ (T is the interbeat interval deviation threshold), the pulse is abnormal.

3. Normal Pulse Segment Count:

If the number of consecutive normal pulses is less than N (N is the normal pulse segment threshold), the segment will be excluded.

4. First Normal Pulse

The first normal pulse after an abnormal pulse is excluded.

Referring still to FIG. 6, an implementation of flowchart 80 will now be described.

A stage S82 of flowchart 80 encompasses a reading a current PPG pulse and a stage S84 of flowchart 80 encompasses a delineation of the fiducial points of the current PPG pulse. A stage S86 of flowchart 80 encompasses a determination of whether all fiducial points were delineated during stage S84. If all fiducial points were not delineated during stage S84, then flowchart 80 proceeds to a stage S88 to read the next PPG pulse if one is available for stages S82 and S84. If all fiducial points were not delineated during stage S84, then flowchart 80 proceeds to a stage S90 to determine if a minimum number of PPG pulses have been read and property delineated to commence with the learning phase.

If the learning phase is not commenced during stage S90, then flowchart 80 proceeds to stage S92 to calculate current running averages of the fiducials and then further proceeds to stage S88 as previously described. If the learning phase is commenced during stage S90, then flowchart 80 proceeds to stage S94 to calculate pulse abnormality scores as previously described herein.

Figure 7:
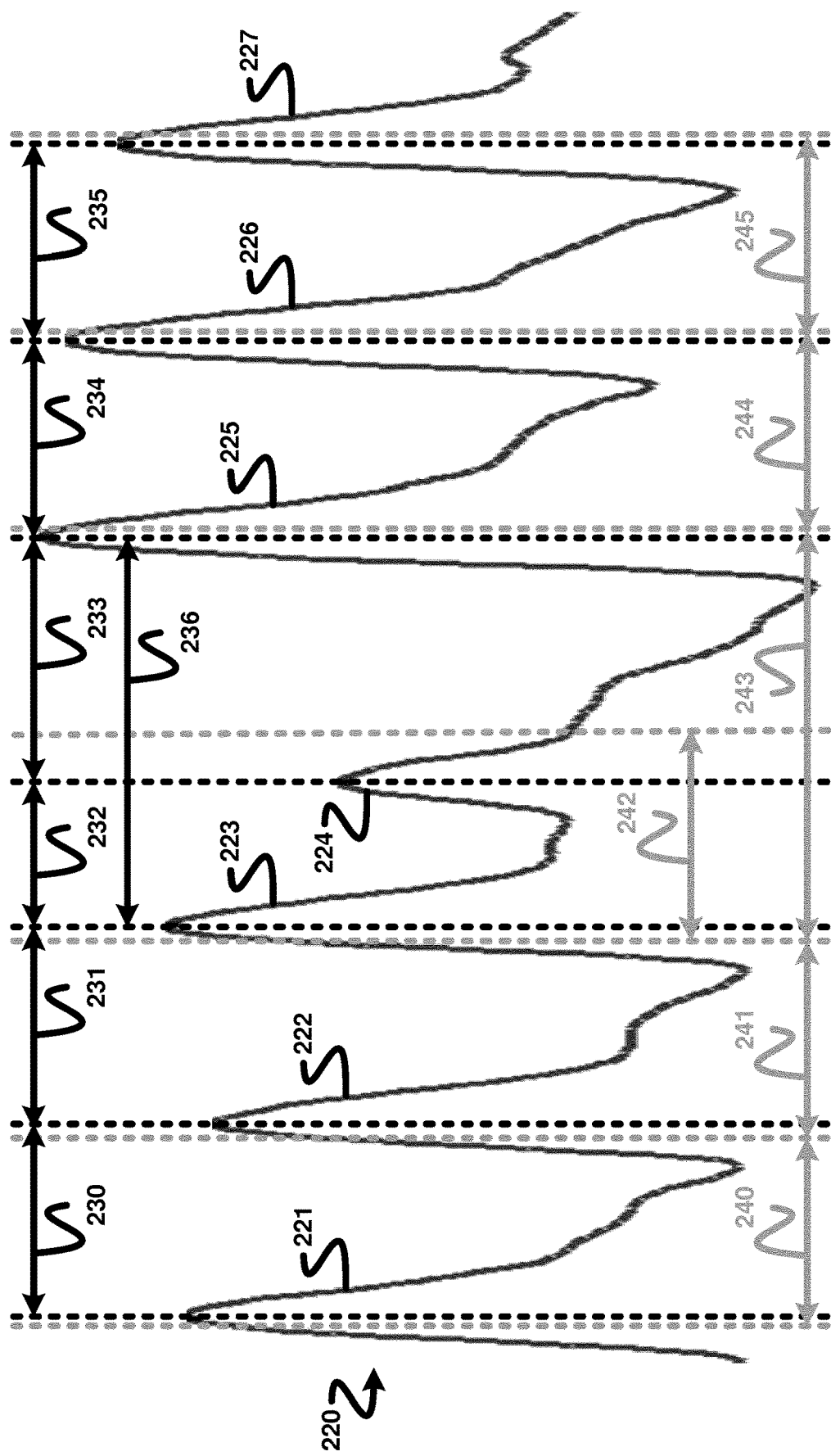
FIG. 7 illustrates a first exemplary abnormal PPG pulse detection based on an interbeat interval criterion in accordance with the inventive principles of the present disclosure.

For example, FIG. 7 illustrates an example of abnormality scoring of a PPG signal 220 in presence of PVC, where the distance of PVC pulse from its predicted location determined by average interbeat interval is more than the threshold ($\Delta>T$), and the pulse is marked abnormal. More particularly, interbeat interval deviation between peak-peak intervals 230, 231, 233, 234 and 235 and respective average peak-peak intervals 240, 241, 244 and 245 are less than the threshold T whereby the associated pulses 221, 222, 223, 226 and 227 are designated as normal. Conversely, an interbeat interval deviation between peak-peak intervals 232 and an average peak-peak intervals 242 is more than the threshold T whereby the associated pulse 224 is are designated as abnormal. Further, in view of pulse 224 being designated as abnormal, an interbeat interval deviation between peak-peak intervals 246 and a twice the average peak-peak intervals 243 is less than the threshold T whereby the associated pulses 223 and 225 will be merged and designated as normal.

Figure 8:
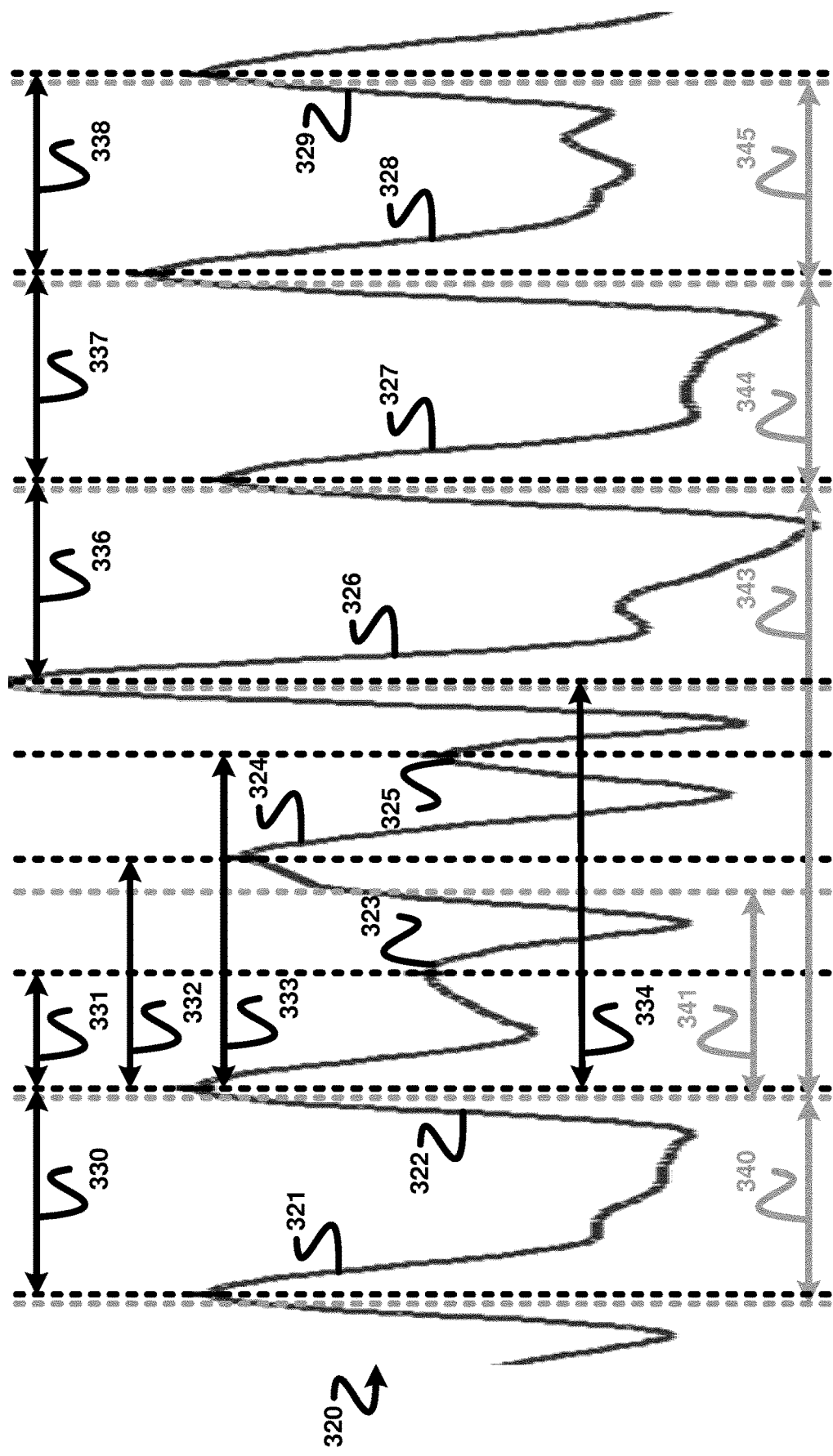
FIG. 8 illustrates a second exemplary abnormal PPG pulse detection based on an interbeat interval criterion in accordance with the inventive principles of the present disclosure.

By further example, FIG. 8 illustrates an example of an abnormality scoring of a PPG signal 230 in artifact-corrupted pulses, where the distance of artifact pulses from their predicted locations determined by the average interbeat interval is more than threshold ($\Delta>T$), and the pulse is marked abnormal. More particularly, interbeat interval deviation between peak-peak intervals 330, 336, 337 and 338 and respective average peak-peak intervals 340, 343, 344 and 345 are less than the threshold T whereby the associated pulses 321, 327, 328 and 329 are designated as normal. Conversely, an interbeat interval deviation between peak-peak intervals of 331, 332, 333 and 334 and an corresponding average peak-peak intervals is more than the threshold T whereby the associated pulse 323, 324 and 325 are designated as abnormal. Further, in view of pulse 323, 324 and 325 being designated as abnormal, an interbeat interval deviation between peak-peak intervals 335 and a twice the average peak-peak intervals 342 is less than the threshold T whereby the associated pulses 322 and 326 will be merged and designated as normal.

Figure 9:
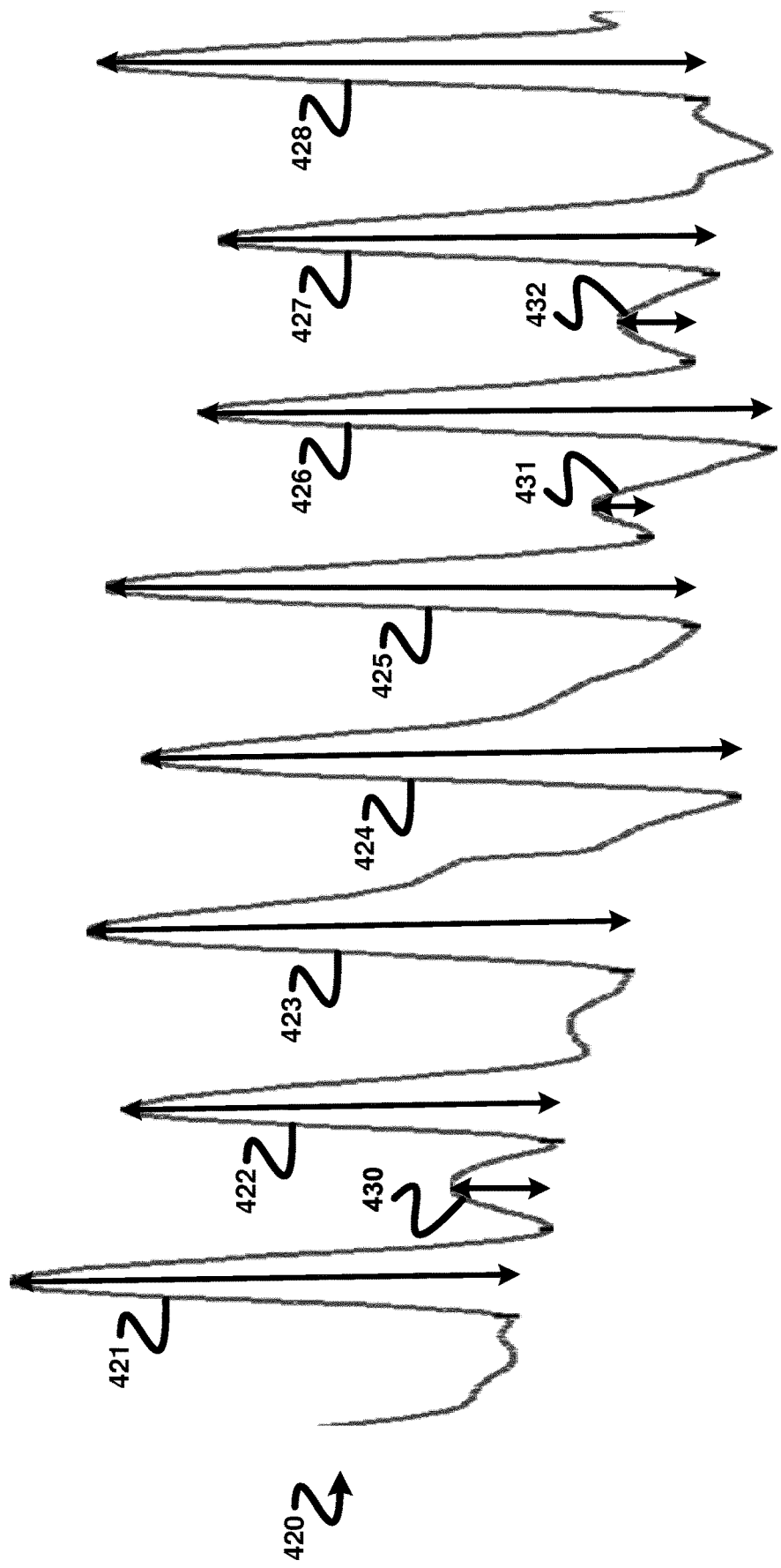
FIG. 9 illustrates a first exemplary abnormal PPG pulse detection based on an amplitude ratio criterion in accordance with the inventive principles of the present disclosure.

By further example, FIG. 9 illustrates an example of abnormality scoring for low-amplitude pulses 430, 431 and 432 where the inverse of ratio of respective pulse amplitudes to its predicted value determined by average PT amplitude is greater than threshold (R=PT avg/PT>M with M=3), and pulses 430, 431 and 432 is marked abnormal. Conversely, abnormality scoring for high-amplitude pulses 421, 422, 423, 426 and 427 where the inverse of ratio of respective pulse amplitudes to its predicted value determined by average PT amplitude is less than threshold (R=PT avg/PT<M with M=3), and pulses 421, 422, 423, 426 and 427 are marked normal. Additionally, abnormality scoring for high-amplitude pulses 424, 425 and 428 where the ratio of respective pulse amplitudes to its predicted value determined by average PT amplitude is less than threshold (R=PT/PT avg<M with M=3), and pulses 424, 425 and 428 are marked normal.

Figure 10:
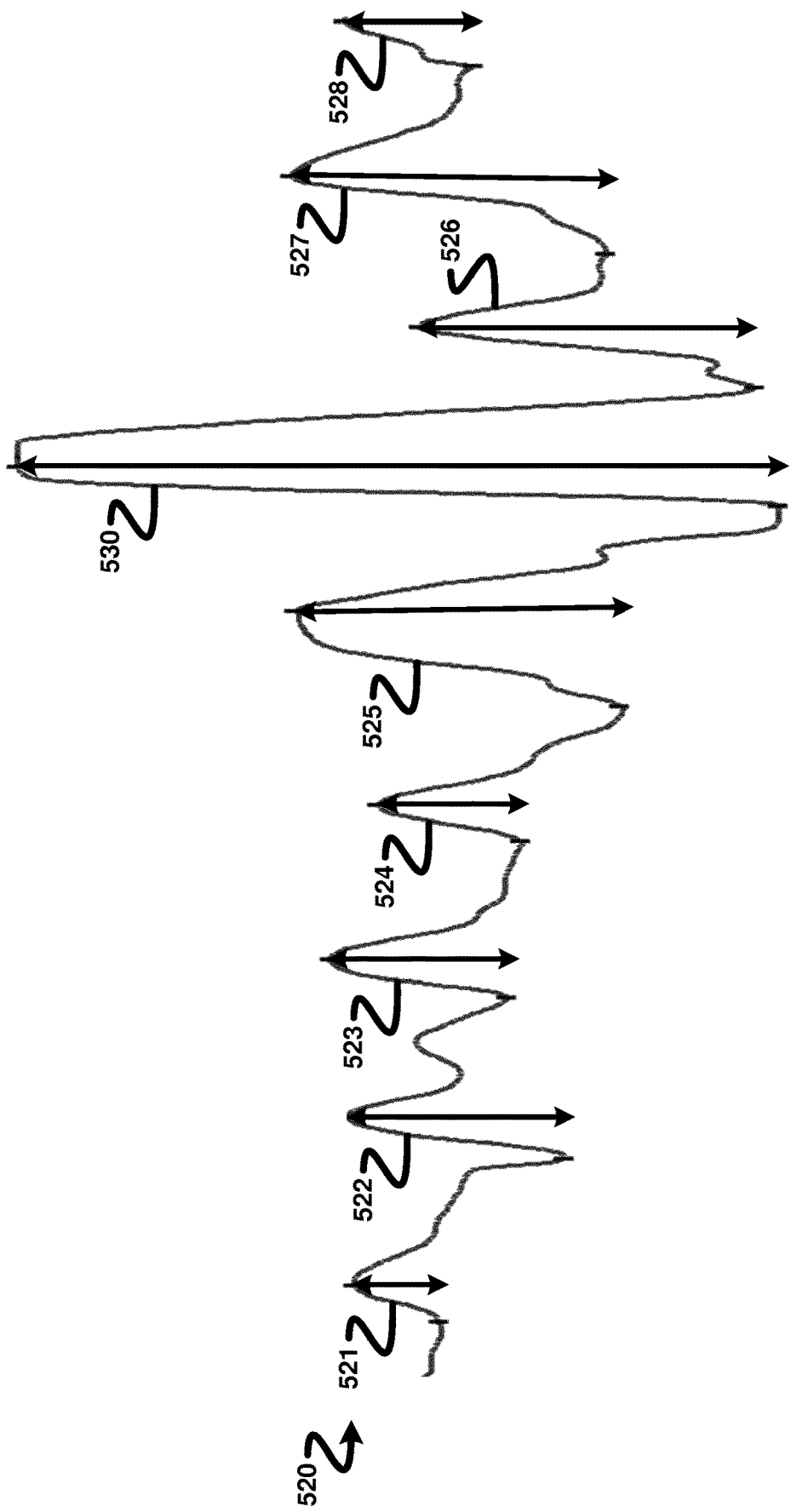
FIG. 10 illustrates a second exemplary abnormal PPG pulse detection based on an amplitude ratio criterion in accordance with the inventive principles of the present disclosure.

By further example, FIG. 10 illustrates an example of abnormality scoring for high-amplitude pulse 530 where the ratio of pulse amplitude to its predicted value determined by average PT amplitude is greater than threshold (R=PT/$PT_{avg}$>M with M=3), and pulse 530 is marked abnormal. Conversely, abnormality scoring for low-amplitude pulses 521, 523, 524 and 528 where the inverse of ratio of respective pulse amplitudes to its predicted value determined by average PT amplitude is less than threshold (R=PT avg/PT<M with M=3), and pulses 521, 523, 524 and 528 are marked normal. Additionally, abnormality scoring for high-amplitude pulses 522, 525, 526 and 527 where the ratio of respective pulse amplitudes to its predicted value determined by average PT amplitude is less than threshold (R=PT/PT avg<M with M=3), and pulses 522, 525, 526 and 527 are marked normal.

Referring back to FIG. 5, a stage S96 of flowchart 80 determines whether a current pulse was designated as normal or abnormal during stage S94. If the current pulse is designated as abnormal during stage S94, then flowchart 80 proceeds to a stage S98 to mark the current pulse as abnormal for extraction and then to a stage S100 to determine whether a normal segment of pulses immediately succeeding the designated abnormal current pulse is short. If the normal segment of pulses are not short, then flowchart 80 proceeds to stage S88 as previously described. If the normal segment of pulses is short, then flowchart 80 proceeds to stage S102 to exclude the normal segment of pulses and thereafter to stage S88 as previously described.

Figure 11:
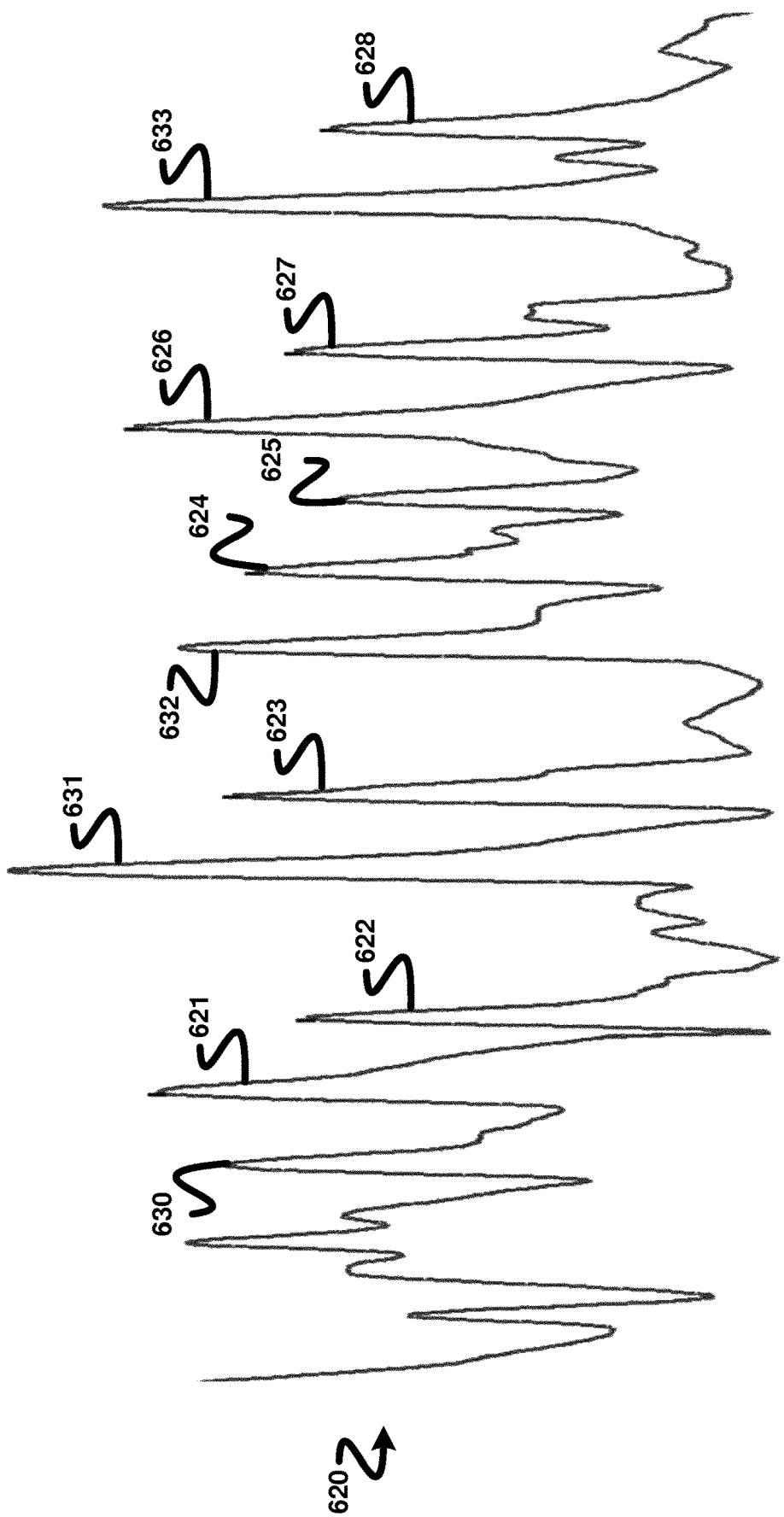
FIG. 11 illustrates an exemplary embodiment of a normalized PPG signal in accordance with the inventive principles of the present disclosure.

For example, FIG. 11 illustrates a pulse 630 and 632 being designated as abnormal, and pulses 621, 622 and 624-627 being designated as normal. As such, the short normal PPG segment of pulses 621 and 622 will be excluded in view of the number of two pulses in the normal pulse segment being less than the normal pulse segment threshold (N=4). Conversely, the short normal PPG segment of pulses 624-627 will not be excluded in view of the number pulses in a normal pulse segment being equal to the normal pulse segment threshold (N=4).

Referring back to FIG. 5, if the current pulse is designated as normal during stage S94, then flowchart 80 proceeds to a stage S104 to mark the current pulse as normal for non-extraction and then to a stage S106 to determine whether the immediate preceding pulse was designated as abnormal. If the immediate preceding pulse was designated as abnormal during stage S104, then flowchart 80 proceeds to a stage S108 to exclude the normal current pulse and thereafter to stage S88 as previously described.

For example, FIG. 11 illustrates a pulse 631 and 633 being designated as abnormal, and pulses 623 and 628 being designated as normal. As such, pulses 623 and 628 will be excluded in view of following designated abnormal pulses 631 and 633.

Referring back to FIG. 5, if the immediate preceding pulse was designated as abnormal during stage S104, then flowchart 80 sequentially proceeds through a stage S110 to calculate fiducial averages of the normal pulses, a stage S112 to calculate the PRV parameter from a HRV measurement of the normal pulses, an optional stage S114 to update the criteria thresholds before and stage S88 as previously described.

More particularly, by finding the normal PPG pulses and their corresponding interbeat intervals, PRV parameters comparable to HRV parameters are able to calculated such For example, HRV parameter pNN50 is a ratio of the number of interbeat interval differences greater than 50 msec in successive pulses to the total number of pulses. The inventions of the present disclosure provide for a PRV pNN50 parameter calculated from PPG measurements to its counterpart calculated from the ECG channel.

Figure 12:
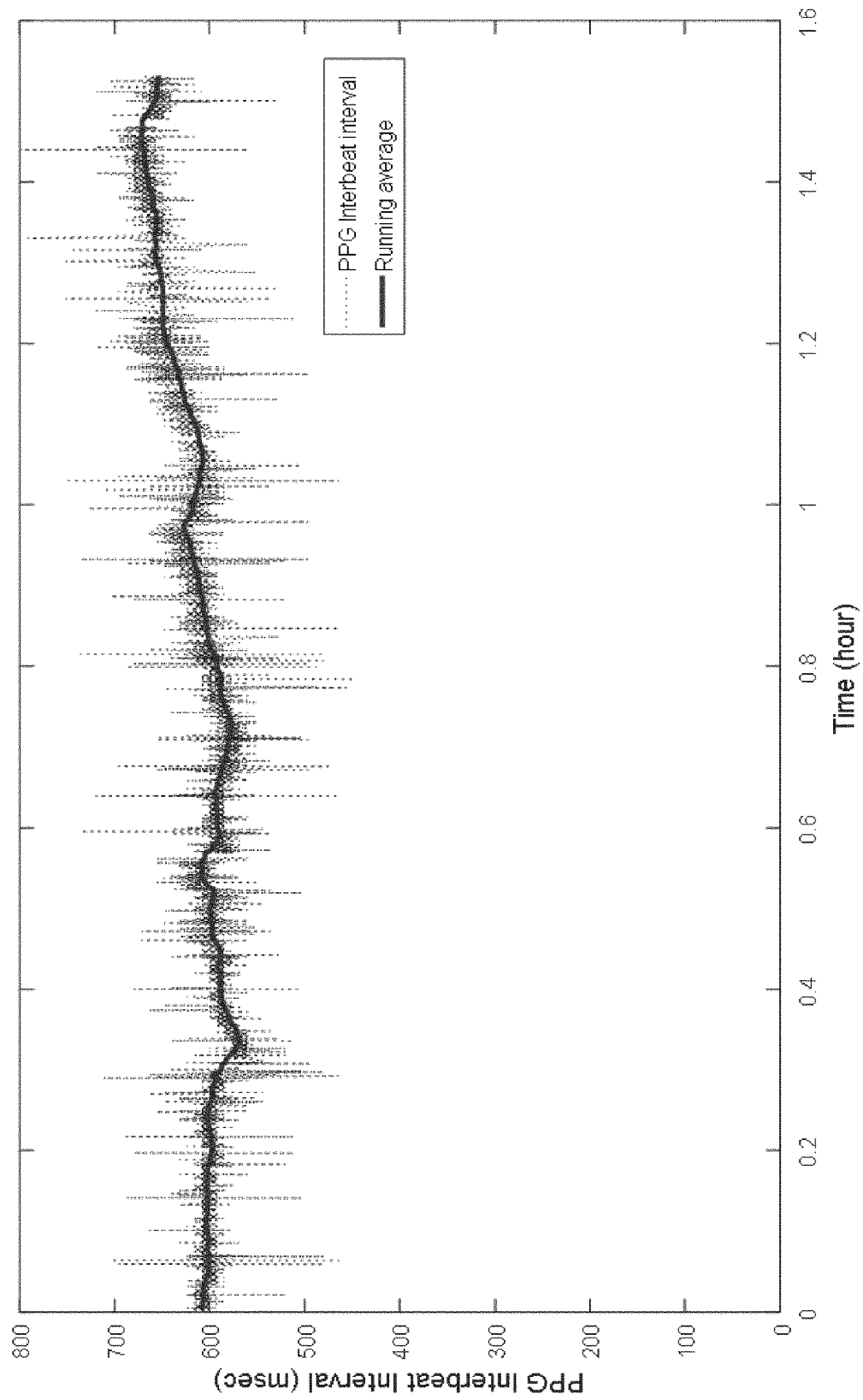
FIG. 12 illustrates a first exemplary PPG interbeat intervals and running averages in accordance with the inventive principles of the present disclosure.
Figure 13:
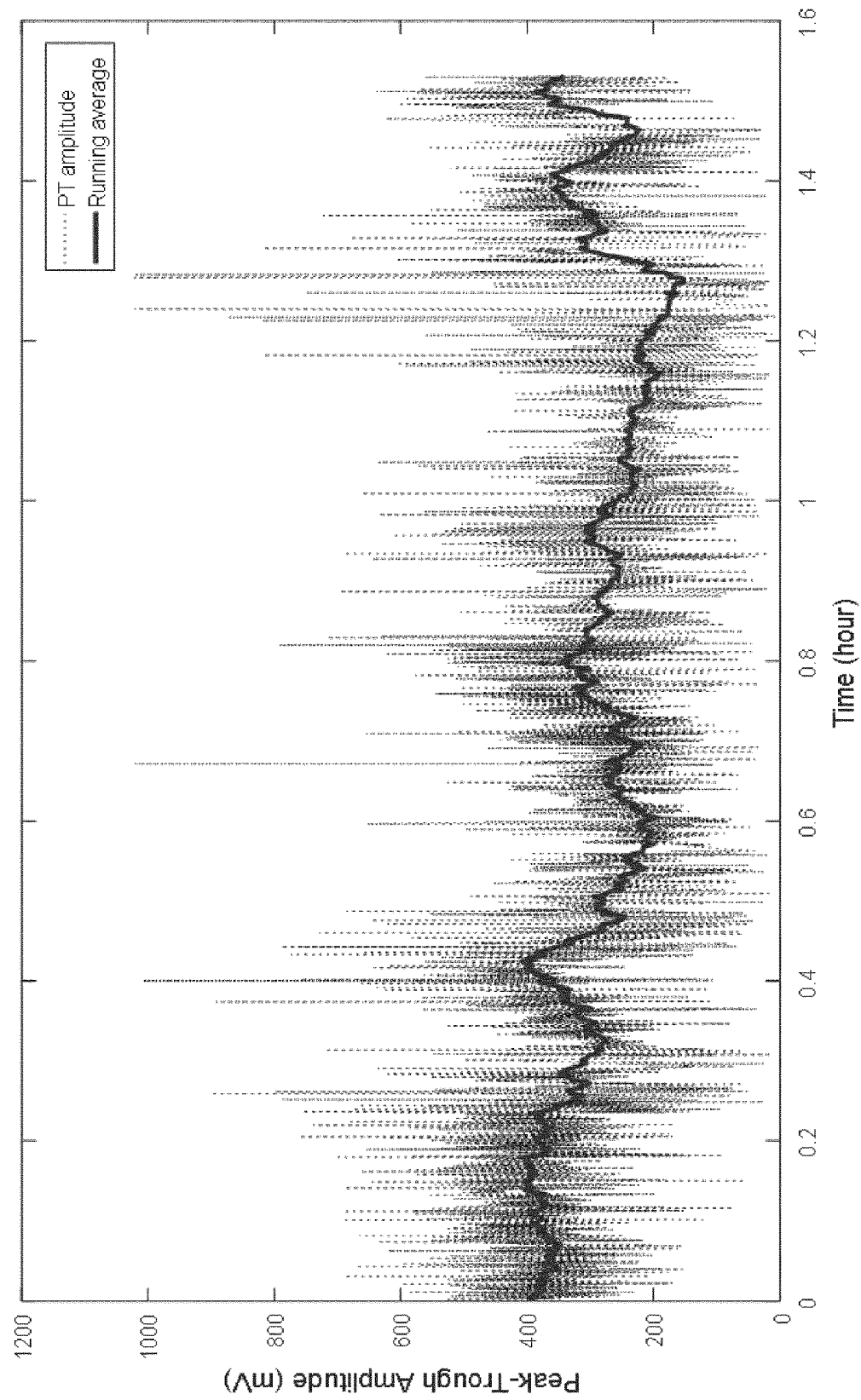
FIG. 13 illustrates a first exemplary PPG fiducial amplitudes and running averages in accordance with the inventive principles of the present disclosure.

For example, in one embodiment, FIGS. 12 and 13 illustrate the instantaneous values and the running averages for PPG interbeat interval and PT amplitude calculated on the normal PPG pulses, and applied in the stage 112. For this embodiment, the optimal thresholds of row 11 with the lowest difference in pNN50 and then higher coverage percentage (T=150 ms, M=1.5, and N=6), for example.

In this example: ECG HRV parameter: pNN50_ECG=0.74.

| Row | T (IBI Threshold) | M (Amplitude threshold) | N (Normal pulses) | pNN50 (%) | Coverage (%) |
|---|---|---|---|---|---|
| 1 | 100 | 1.5 | 12 | 0.49 | 23.2 |
| 2 | 100 | 1.5 | 6 | 0.42 | 26.9 |
| 3 | 100 | 1.5 | 3 | 0.38 | 30.1 |
| 4 | 100 | 2.0 | 12 | 0.90 | 36.6 |
| 5 | 100 | 2.0 | 6 | 0.93 | 39.0 |
| 6 | 100 | 2.0 | 3 | 0.95 | 42.0 |
| 7 | 100 | 3.0 | 12 | 1.11 | 44.2 |
| 8 | 100 | 3.0 | 6 | 1.34 | 47.4 |
| 9 | 100 | 3.0 | 3 | 1.44 | 50.6 |
| 10 | 150 | 1.5 | 12 | 0.48 | 23.6 |
| 11 | 150 | 1.5 | 6 | 0.71 | 27.4 |
| 12 | 150 | 1.5 | 3 | 0.63 | 30.7 |
| 13 | 150 | 2.0 | 12 | 1.14 | 39.0 |
| 14 | 150 | 2.0 | 6 | 1.63 | 42.6 |
| 15 | 150 | 2.0 | 3 | 1.78 | 45.8 |
| 16 | 150 | 3.0 | 12 | 1.68 | 44.7 |
| 17 | 150 | 3.0 | 6 | 2.39 | 48.5 |
| 18 | 150 | 3.0 | 3 | 2.68 | 52.2 |
| 19 | 200 | 1.5 | 12 | 0.75 | 24.1 |
| 20 | 200 | 1.5 | 6 | 0.92 | 28.4 |
| 21 | 200 | 1.5 | 3 | 0.86 | 31.6 |
| 22 | 200 | 2.0 | 12 | 1.81 | 40.2 |
| 23 | 200 | 2.0 | 6 | 2.15 | 43.3 |
| 24 | 200 | 2.0 | 3 | 2.37 | 46.5 |
| 25 | 200 | 3.0 | 12 | 2.66 | 44.9 |
| 26 | 200 | 3.0 | 6 | 3.89 | 49.0 |
| 27 | 200 | 3.0 | 3 | 4.33 | 52.2 |

Table 1 illustrates an exemplary embodiment of the present disclosure using for this example a set of different thresholds. The optimal thresholds are selected at T=150 ms, M=1.5, and N=6 where pNN50 has the lowest difference between ECG and PPG and then the coverage percentage is higher than other configurations.

A second example of an exemplary embodiment of the present disclosure can use a single-channel PPG 3 hours and 55 minutes long, with higher PPG signal quality in most areas and no PVC pulses is presented here.

Figure 14:
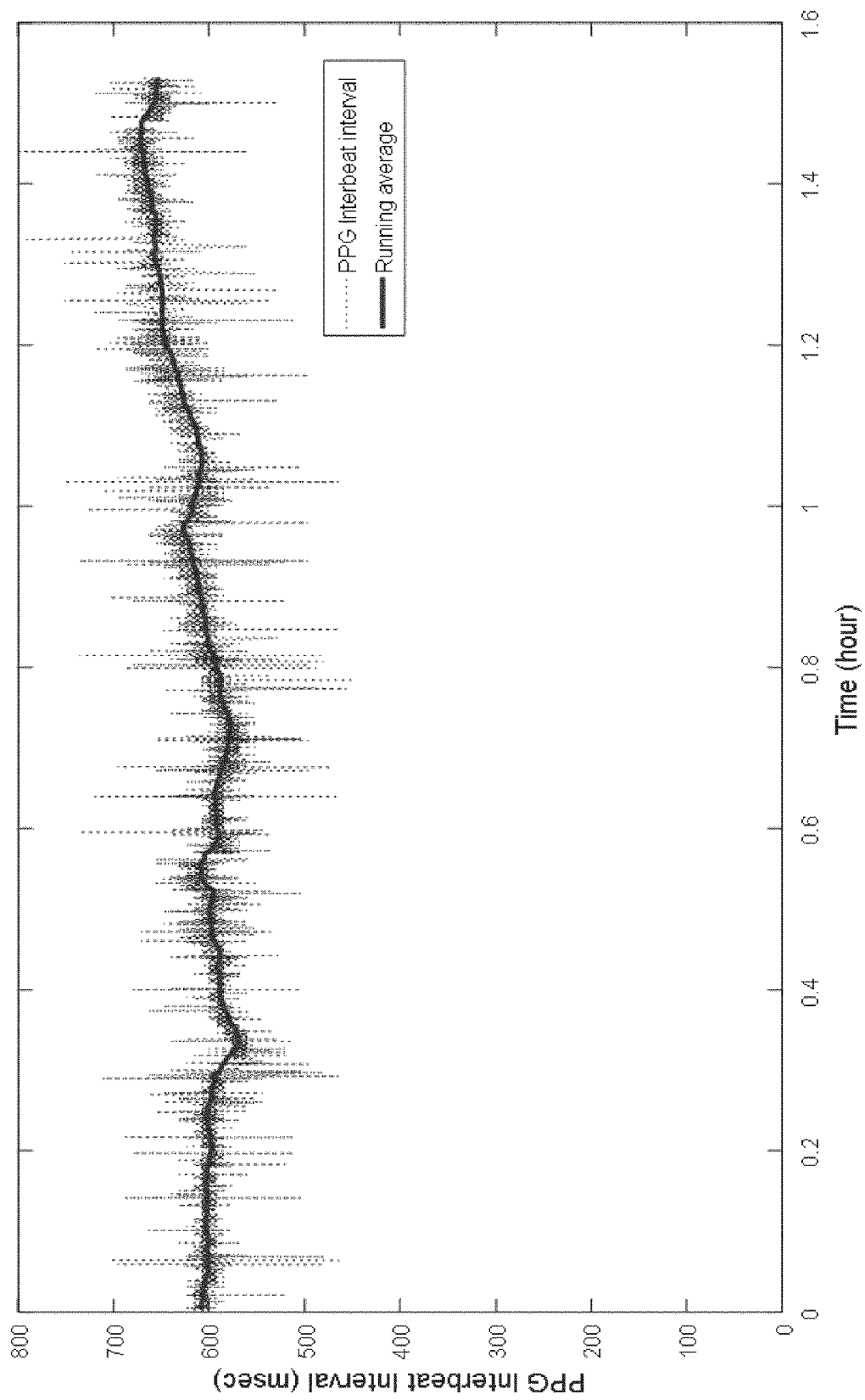
FIG. 14 illustrates a second exemplary PPG interbeat intervals and running averages in accordance with the inventive principles of the present disclosure.
Figure 15:
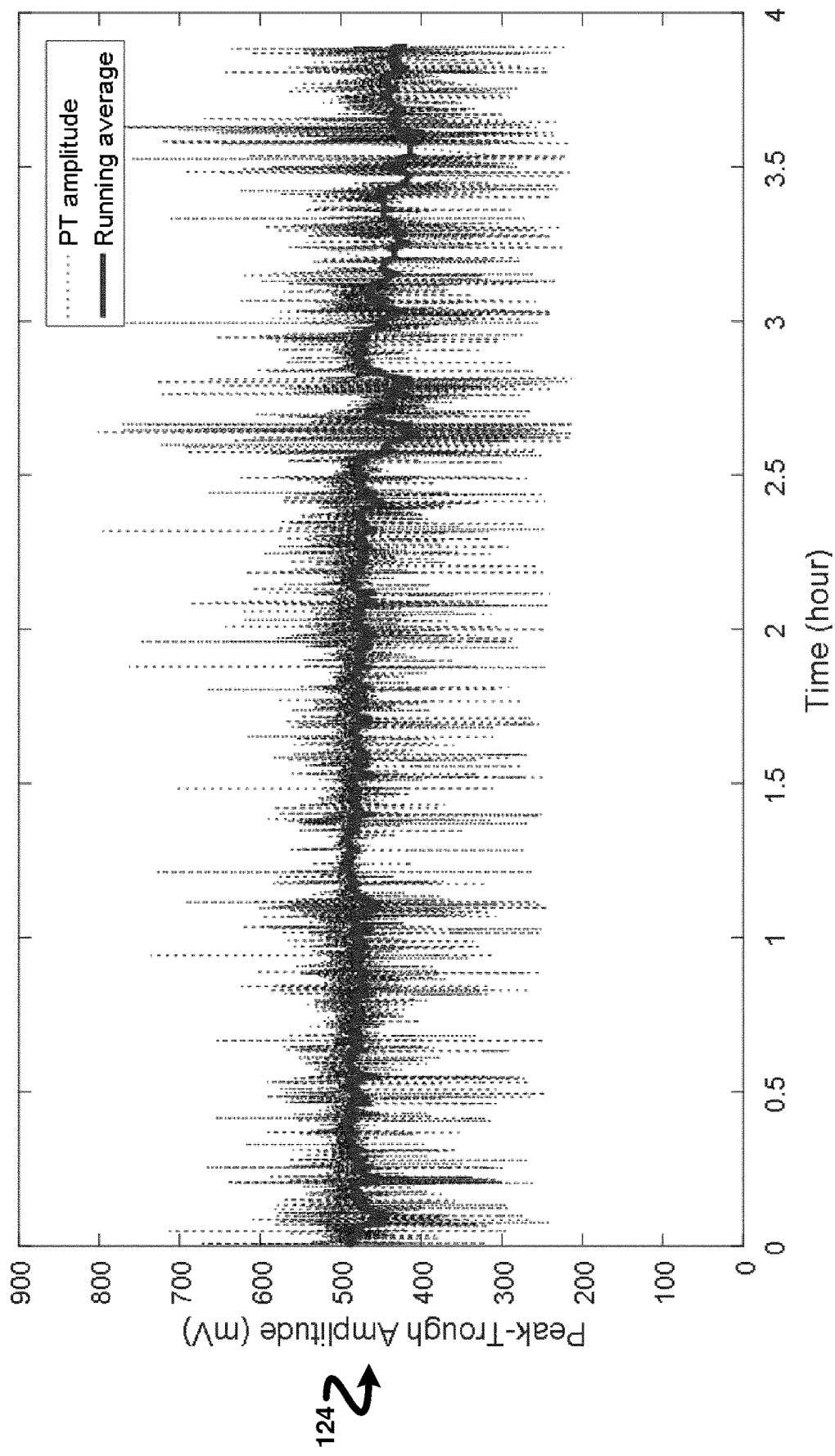
FIG. 15 illustrates a second exemplary PPG fiducial amplitudes and running averages in accordance with the inventive principles of the present disclosure.

FIGS. 14 and 15 illustrate the instantaneous values and the running averages for PPG interbeat interval and PT amplitude calculated on the normal PPG pulses, and applied in the analysis, in accordance this embodiment of the present disclosure.

Exemplary embodiments of the present disclosure can use a set of different thresholds as in Table 2, for example. Exemplary embodiments of the present disclosure can choose the optimal thresholds row 7 with the lowest difference in pNN50 between ECG and PPG and then higher coverage percentage (T=100 ms, M=3.0, and N=12), for example. In this example, ECG HRV parameter: pNN50 ECG=0.32.

| Row | T (IBI Threshold) | M (Amplitude threshold) | N (Normal pulses) | pNN50 (%) | Coverage (%) |
|---|---|---|---|---|---|
| 1 | 100 | 1.5 | 12 | 0.17 | 76.8 |
| 2 | 100 | 1.5 | 6 | 0.20 | 77.7 |
| 3 | 100 | 1.5 | 3 | 0.20 | 78.1 |
| 4 | 100 | 2.0 | 12 | 0.27 | 80.8 |
| 5 | 100 | 2.0 | 6 | 0.29 | 81.2 |
| 6 | 100 | 2.0 | 3 | 0.29 | 81.7 |
| 7 | 100 | 3.0 | 12 | 0.32 | 81.3 |
| 8 | 100 | 3.0 | 6 | 0.34 | 81.8 |
| 9 | 100 | 3.0 | 3 | 0.35 | 82.3 |
| 10 | 150 | 1.5 | 12 | 0.25 | 77.3 |
| 11 | 150 | 1.5 | 6 | 0.31 | 78.6 |
| 12 | 150 | 1.5 | 3 | 0.36 | 79.2 |
| 13 | 150 | 2.0 | 12 | 0.37 | 81.1 |
| 14 | 150 | 2.0 | 6 | 0.42 | 82.1 |
| 15 | 150 | 2.0 | 3 | 0.45 | 82.6 |
| 16 | 150 | 3.0 | 12 | 0.42 | 81.8 |
| 17 | 150 | 3.0 | 6 | 0.51 | 82.8 |
| 18 | 150 | 3.0 | 3 | 0.54 | 83.2 |
| 19 | 200 | 1.5 | 12 | 0.66 | 79.2 |
| 20 | 200 | 1.5 | 6 | 0.88 | 80.5 |
| 21 | 200 | 1.5 | 3 | 1.13 | 81.4 |
| 22 | 200 | 2.0 | 12 | 0.99 | 83.1 |
| 23 | 200 | 2.0 | 6 | 1.23 | 84.2 |
| 24 | 200 | 2.0 | 3 | 1.52 | 85.1 |
| 25 | 200 | 3.0 | 12 | 1.04 | 84.0 |
| 26 | 200 | 3.0 | 6 | 1.34 | 85.3 |
| 27 | 200 | 3.0 | 3 | 1.67 | 86.2 |

Table 2 illustrates an exemplary embodiment of the present disclosure using for this example a set of different thresholds. The optimal thresholds are selected at T=100 ms, M=3.0, and N=12 where pNN50 has the lowest difference between ECG and PPG and then the coverage percentage is higher than other configurations.

Figure 16:
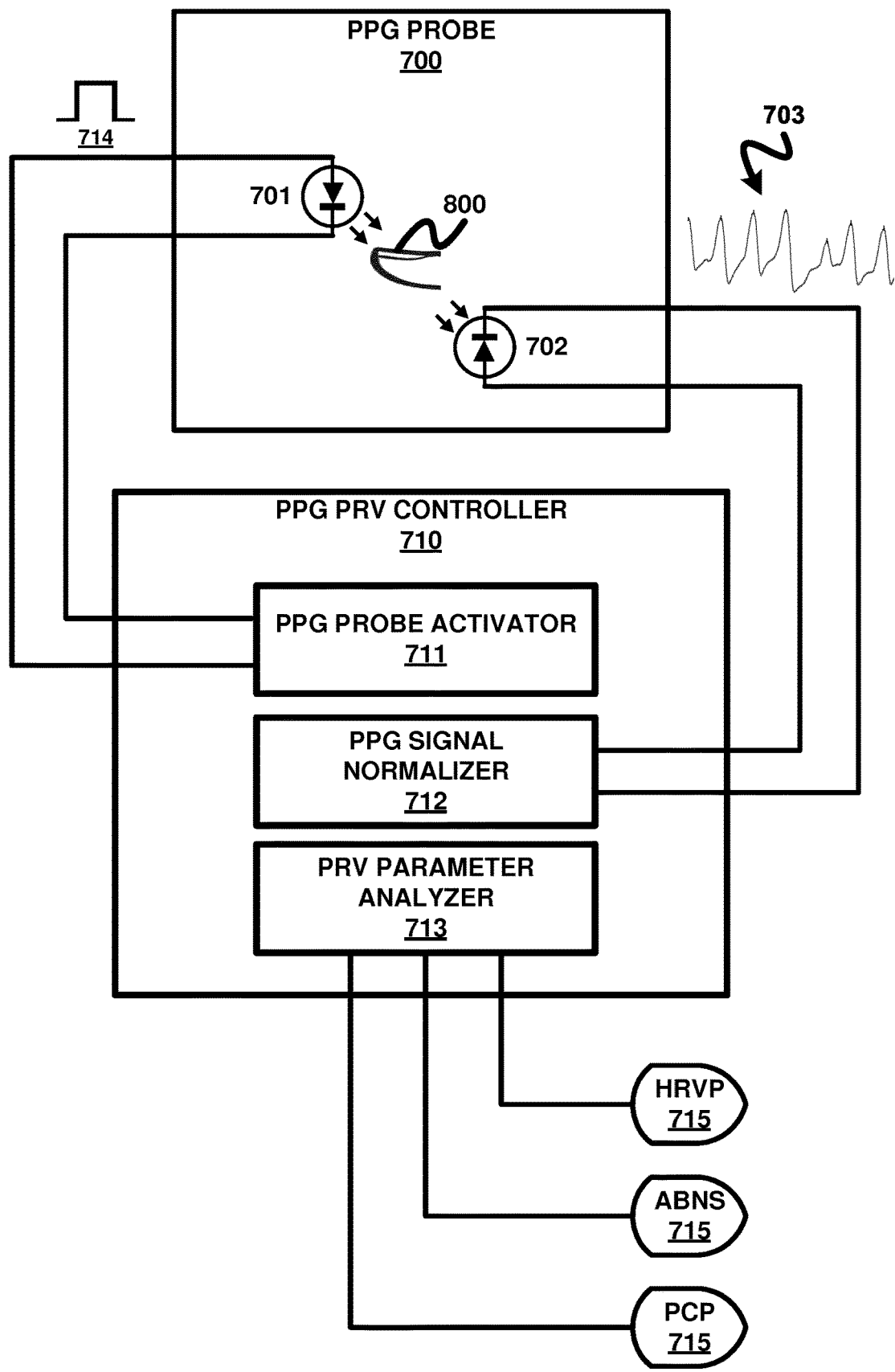
FIG. 16 an exemplary embodiment of a PPG signal device in accordance with the inventive principles of the present disclosure.
Figure 17:
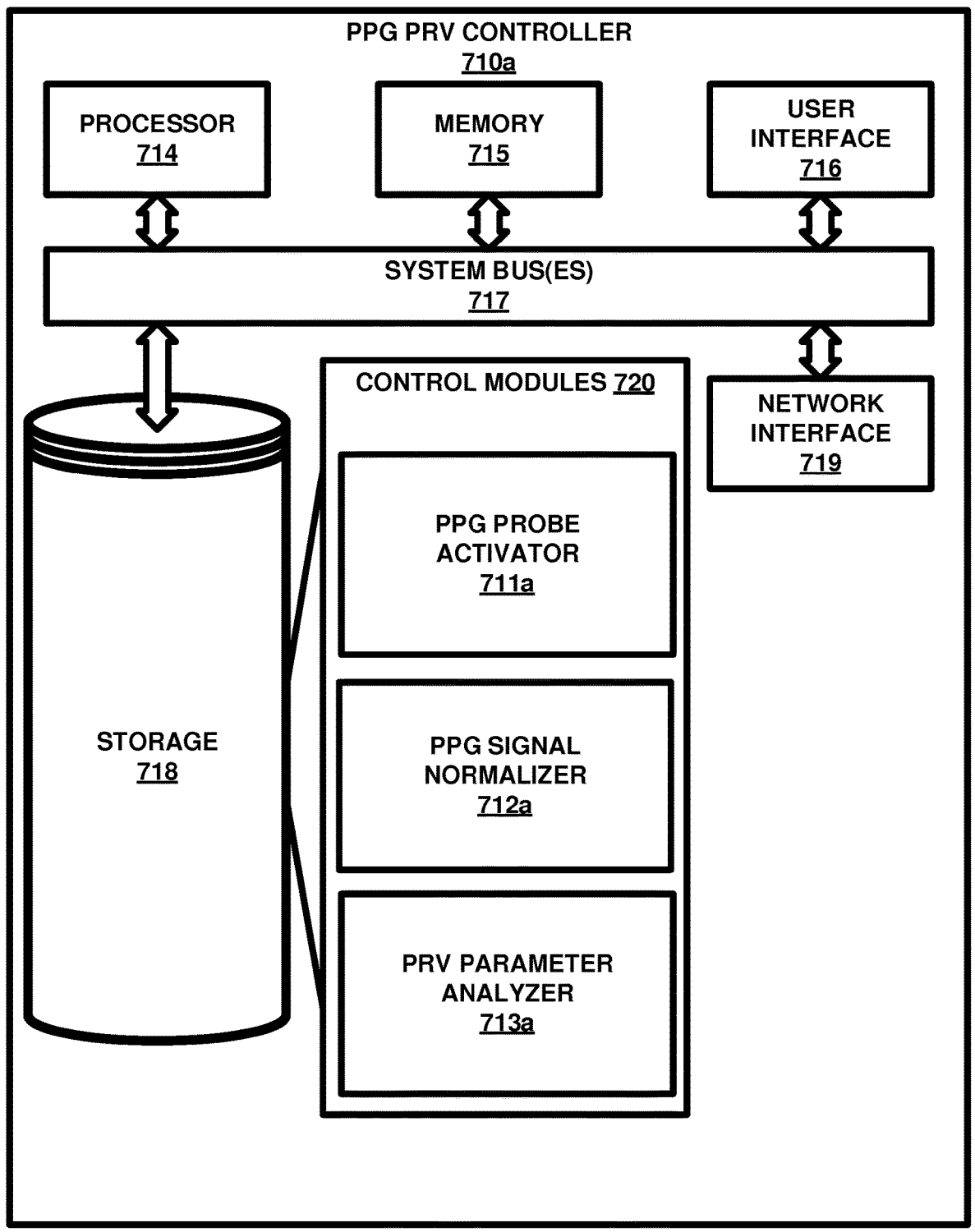
FIG. 17 an exemplary embodiment of a PPG PRV controller in accordance with the inventive principles of the present disclosure.

To facilitate an understanding of the various inventions of the present disclosure, the following description of FIGS. 16 and 17 teaches basic inventive principles of an embodiment of a PPG PRV device for generating a PRV parameter of a PPG signal as an estimation of a HRV parameter of an ECG signal in accordance with the present disclosure. From this description, those having ordinary skill in the art will appreciate how to apply the inventive principles of the present disclosure of additional embodiments of PPG PRV devices generating a PRV parameter of a PPG signal as an estimation of a HRV parameter of an ECG signal in accordance with the present disclosure.

Generally, as one having ordinary skill in the art shall appreciate in view of the teachings provided herein, exemplary embodiments of the present disclosure can be implemented, deployed or otherwise used in or with any PPG device collecting at least one channel of PPG waveform. Examples of such PPG devices include Philips Intellivue Guardian Solution with wearable wireless patch, activity monitoring watches such as Actiwatch and HealthWatch, as well as home sleep monitoring devices such as Alice PDx, for example. This list of PPG devices and related applications is in no way intended to be limiting, but rather just provided to be a sample and example of the types of devices and applications in/with which exemplary embodiments of the present disclosure can be used, including devices and applications known today and to be known in the future.

In one embodiment, as shown in FIG. 16, a PPG PVR device of the present disclosure employs a PPG probe 700 as known the art of the present disclosure including a light emitter 702 and a light detector 702 for generating a PPG signal 703 of an anatomy (e.g., a finger 800 as shown, or an ear, wrist or forehead) via an activation of light emitter 702 by an activation signal 714.

The PPG PVR device of the present disclosure further employs PPG PRV controller 710 including modules in the form of a PPG probe activator 711 for activating PPG probe 700 as known in the art of the present disclosure, a PPG signal normalizer 721 for normalizing PPG signal 703 as previously described in the present disclosure and a PVR parameter analyzer 713 for deriving a PRV parameter from a HRV measurement of the normalized PPG signal 703 as previously described in the present disclosure.

In one embodiment, as shown in FIG. 17, controller 710*a* includes a processor 714, a memory 715, a user interface 716, a network interface 719, and a storage 718 interconnected via one or more system bus(es) 717. In practice, the actual organization of the components 714-718 of controller 710*a* may be more complex than illustrated.

The processor 714 may be any hardware device capable of executing instructions stored in memory or storage or otherwise processing data. As such, the processor 714 may include a microprocessor, field programmable gate array (FPGA), application-specific integrated circuit (ASIC), or other similar devices.

The memory 715 may include various memories such as, for example L1, L2, or L3 cache or system memory. As such, the memory 715 may include static random access memory (SRAM), dynamic RAM (DRAM), flash memory, read only memory (ROM), or other similar memory devices.

The user interface 716 may include one or more devices for enabling communication with a user such as an administrator. For example, the user interface 716 may include a display, a mouse, and a keyboard for receiving user commands. In some embodiments, the user interface 716 may include a command line interface or graphical user interface that may be presented to a remote terminal via the network interface 719.

The network interface 719 may include one or more devices for enabling communication with other hardware devices. For example, the network interface 719 may include a network interface card (NIC) configured to communicate according to the Ethernet protocol. Additionally, the network interface 719 may implement a TCP/IP stack for communication according to the TCP/IP protocols. Various alternative or additional hardware or configurations for the network interface will be apparent.

The storage 718 may include one or more machine-readable storage media such as read-only memory (ROM), random-access memory (RAM), magnetic disk storage media, optical storage media, flash-memory devices, or similar storage media. In various embodiments, the storage 718 may store instructions for execution by the processor 714 or data upon with the processor 714 may operate. For example, the storage 718 store a base operating system (not shown) for controlling various basic operations of the hardware.

More particular to the present disclosure, storage 718 further stores control modules 720 including PPG probe activator 711*a*, PPG signal normalizer 712*a* and PRV parameter analyzer 713*a*.

The present disclosure disclosed herein has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Further, as one having ordinary skill in the art shall appreciate in view of the teachings provided herein, features, elements, components, etc. disclosed and described in the present disclosure/specification and/or depicted in the appended Figures may be implemented in various combinations of hardware and software, and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and exemplary embodiments of the present disclosure, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar functionality, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having disclosed and described preferred and exemplary embodiments of the present disclosure (which embodiments are intended to be illustrative and not limiting), it is noted that modifications and variations can be made by persons having ordinary skill in the art in view of the teachings provided herein, including the appended Figures and claims. It is therefore to be understood that changes can be made in/to the preferred and exemplary embodiments of the present disclosure which are within the scope of the present disclosure and exemplary embodiments disclosed and described herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

Exemplary Experiment, Test and Study: The following exemplary experiment, test and study is provided as an example in accordance with an exemplary embodiment of the present disclosure. The following is provided and intended to be illustrative and not limiting to the scope of the present disclosure.

Background of the study: The feasibility of using photoplethysmography (PPG) for analyzing heart rate variability (HRV) has been the subject of many recent studies with contradicting results. The contradiction is partially because analyzing HRV needs accurate measurement of cardiac cycles which is more challenging in PPG than ECG due to its inherent characteristics such as the smoothness of waveform and higher susceptibility to motion artifact. To handle the motion artifact, some devices use accelerometers to disable analysis during regions of high or even moderate activity, but such sensors are not always available. Many published PPG-based HRV studies are limited to results from clean motion-free data of healthy subjects in ideal experimental settings. We, however, have developed system, device and method using a PPG-only algorithm to analyze HRV on real-life high-risk in-hospital ICU patients. In this study, we compare the results of exemplary embodiment of the present disclosure to those from simultaneously recorded ECG.

Exemplary method: Exemplary embodiment of the present disclosure analyzes the waveform morphology to detect artifact and abnormal rhythms in order to select clean intervals with a high probability of representing the underlying cardiac cycle. The HRV parameters are then calculated using these intervals. Three fiducial points are automatically marked on each PPG pulse in the single-channel PPG waveforms, and the median of the three intervals (trough-trough, upslope-upslope, and peak-peak between consecutive beats) is used as the interbeat interval for HRV analysis. A large subset of the MIMIC II database was used for evaluation. ECG intervals were measured from the R-wave peaks.

Exemplary results: Several time-domain HRV parameters were calculated using the ECG and PPG data from 330,670 recordings in the database (total of 238,284 hours). For ECG and PPG, respectively, the average mean NN values were 715.6 ms and 718.5 ms, average SDNN values were 29.0 ms and 28.8 ms, and average SDSD values were 16.8 ms and 20.6 ms. Distributions of the pNN50 parameter from ECG and PPG are summarized in table below.

| | pNN50 (%) | | | | | | | | | | |
|---|---|---|---|---|---|---|---|---|---|---|---|
| | 0-5 | 5-10 | 10-15 | 15-20 | 20-25 | 25-30 | 30-35 | 35-40 | 40-45 | 45-50 | 50-100 |
| ECG (%) | 81.5 | 6.5 | 3.5 | 2.1 | 1.5 | 1.3 | 1.2 | 1.1 | 0.7 | 0.3 | 0.3 |
| PPG (%) | 77.2 | 9.2 | 4.2 | 2.5 | 1.8 | 1.4 | 1.3 | 1.1 | 0.7 | 0.3 | 0.3 |

Exemplary conclusion: We have shown that exemplary embodiment of the present disclosure using a PPG-only algorithm with integrated detection and rejection of abnormal intervals can have a performance comparable to ECG-based HRV analysis on in-hospital ICU patients. On this database, exemplary embodiment of the present disclosure reported only 4.3% more PPG recordings than ECG with a pNN50 value above 5%. This number was 1.6% for the pNN50 above 10%, and 0.9% for pNN50 above 15%.

The invention claimed is:

1. A PPG PRV device for generating a PRV parameter of a PPG signal as an estimation of a HRV parameter of an ECG signal, the PPG PRV device comprising:
   a PPG probe operable to generate the PPG signal; and
   a PPG PRV controller operable in signal communication with the PPG probe to receive the PPG signal, the PPG PRV controller is configured to:
      generate a normalized PPG signal including a plurality of pulses of the PPG signal designated as normal pulses by the PPG PRV controller and excluding at least one pulse of the PPG signal designated as at least one abnormal pulse by the PPG PRV controller, wherein the normalized PPG signal is HRV comparable to the ECG signal;
      derive the PRV parameter from a HRV measurement of the normalized PPG signal; and
      generate an estimation of an HRV parameter of the ECG signal.

2. The PPG PRV device of claim 1, wherein PPG PRV controller is further configured to:
   control a generation of the PPG signal by the PPG probe.

3. The PPG PRV device of claim 1, wherein the PPG PRV controller is further configured to:
   designate a current pulse of the PPG signal as a normal pulse or as an abnormal pulse based on an interbeat interval of each pulse of the PPG signal as delineated by at least one fiducial of each pulse of the PPG signal.

4. The PPG PRV device of claim 1, wherein the PPG PRV controller is configured to:
   generate an interbeat interval deviation as a differential between an interbeat interval of the current pulse of the PPG signal and an average of the interbeat intervals of the pulses of the PPG signal; and
   compare the interbeat interval deviation to an interbeat interval deviation threshold as at least one basis for designating the current pulse of the PPG signal as the normal pulse or the abnormal pulse.

5. The PPG PRV device of claim 1, wherein the PPG PRV controller is further configured to:
   designate a current pulse of the PPG signal as a normal pulse or an abnormal pulse based on an amplitude of each pulse of the PPG signal as delineated by at least two fiducials of each pulse of the PPG signal.

6. The PPG PRV device of claim 5, wherein the PPG PRV controller is further configured to:
   generate an amplitude ratio as quotient between the amplitude of the current pulse of the PPG signal and an average of amplitudes of the pulses of the PPG signal; and
   compare the amplitude ratio to an amplitude ratio threshold as at least one basis for designating the current pulse of the PPG signal as the normal pulse or the abnormal pulse.

7. The PPG PRV device of claim 1, wherein the PPG PRV controller is configured to: exclude, from the normalized PPG signal, a designated normal pulse of the PPG signal based on a count of consecutive designated normal pulses of the PPG signal sequentially succeeding a designated abnormal pulse of the PPG signal being less than a normal pulse segment threshold.

8. The PPG PRV device of claim 1, wherein the PPG PRV controller is configured to: exclude, from the normalized PPG signal, a designated normal pulse of the PPG signal sequentially succeeding a designated abnormal pulse of the PPG signal.

9. A PPG PRV controller for generating a PRV parameter of a PPG signal as an estimation of a HRV parameter of an ECG signal, the PPG PRV controller comprising:
   a PPG signal normalizer configured to generate a normalized PPG signal including a plurality of pulses of the PPG signal designated as normal pulses by the PPG PRV controller and excluding at least one pulse of the PPG signal designated as at least one abnormal pulse by the PPG PRV controller, wherein the normalized PPG signal is HRV comparable to the ECG signal; and
   a PRV parameter analyzer configured to derive the PRV parameter from a HRV measurement of the normalized PPG signal and to estimate an HRV parameter of the ECG signal.

10. The PPG PRV controller of claim 9, wherein the PPG signal normalizer is further configured to:
    designate a current pulse of the PPG signal as a normal pulse or as an abnormal pulse based on an interbeat interval of each pulse of the PPG signal as delineated by at least one fiducial of each pulse of the PPG signal.

11. The PPG PRV controller of claim 10, wherein the PPG signal normalizer is configured to:
    generate an interbeat interval deviation as a differential between an interbeat interval of the current pulse of the PPG signal and an average of the interbeat intervals of the pulses of the PPG signal; and
    compare the interbeat interval deviation to an interbeat interval deviation threshold as at least one basis for designating the current pulse of the PPG signal as the normal pulse or the abnormal pulse.

12. The PPG PRV controller of claim 9, wherein the PPG signal normalizer is further configured to:
    designate a current pulse of the PPG signal as a normal pulse or an abnormal pulse based on an amplitude of each pulse of the PPG signal as delineated by at least two fiducials of each pulse of the PPG signal.

13. The PPG PRV device of claim 1, wherein the PPG signal normalizer is further configured to:
    generate an amplitude ratio as quotient between the amplitude of the current pulse of the PPG signal and an average of amplitudes of the pulses of the PPG signal; and
    compare the amplitude ratio to an amplitude ratio threshold as at least one basis for designating the current pulse of the PPG signal as the normal pulse or the abnormal pulse.

14. The PPG PRV controller of claim 9, wherein the PPG signal normalizer is configured to:
exclude, from the normalized PPG signal, a designated normal pulse of the PPG signal based on a count of consecutive designated normal pulses of the PPG signal sequentially succeeding a designated abnormal pulse of the PPG signal being less than a normal pulse segment threshold.

15. The PPG PRV controller of claim 9, wherein the PPG signal normalizer is configured to:
exclude, from the normalized PPG signal, a designated normal pulse of the PPG signal sequentially succeeding a designated abnormal pulse of the PPG signal.

16. A PPG PRV method for generating a PRV parameter of a PPG signal as an estimation of a HRV parameter of an ECG signal, the PPG PRV method comprising:
generating, by a PPG PRV controller, a normalized PPG signal including a plurality of pulses of the PPG signal designated as normal pulses by the PPG PRV controller and excluding at least one pulse of the PPG signal designated as at least one abnormal pulse by the PPG PRV controller, wherein the normalized PPG signal (20') is HRV comparable to the ECG signal; and
deriving, by the PPG PRV controller, the PRV parameter from a HRV measurement of the normalized PPG signal.

17. The PPG PRV method of claim 16, wherein the generating of the normalized PPG signal includes:
delineating an interbeat interval of each pulse of the PPG signal as delineated by at least one fiducial of each pulse of the PPG signal;
generating an interbeat interval deviation as a differential between an interbeat interval of a current pulse of the PPG signal and an average of the interbeat intervals of the pulses of the PPG signal; and
compare the interbeat interval deviation to an interbeat interval deviation threshold as at least one basis for designating the current pulse of the PPG signal as a normal pulse or as an abnormal pulse.

18. The PPG PRV controller of claim 16, wherein the generating of the normalized PPG signal includes:
delineating an amplitude of each pulse of the PPG signal by at least two fiducials of each pulse of the PPG signal;
generating an amplitude ratio as quotient between the amplitude of a current pulse of the PPG signal and an average of amplitudes of the pulses of the PPG signal; and
compare the amplitude ratio to an amplitude ratio threshold as at least one basis for designating the current pulse of the PPG signal as a normal pulse or as an abnormal pulse.

19. The PPG PRV controller of claim 16, wherein the generating of the normalized PPG signal includes:
excluding, from the normalized PPG signal, a designated normal pulse of the PPG signal based on a count of consecutive designated normal pulses of the PPG signal sequentially succeeding a designated abnormal pulse of the PPG signal being less than a normal pulse segment threshold.

20. The PPG PRV controller of claim 16, wherein the generating of the normalized PPG signal includes:
excluding, from the normalized PPG signal, a designated normal pulse of the PPG signal sequentially succeeding a designated abnormal pulse of the PPG signal.

* * * * *